(12) United States Patent
Zemach et al.

(10) Patent No.: US 11,730,133 B2
(45) Date of Patent: *Aug. 22, 2023

(54) HIGH YIELD SESAME

(71) Applicant: EQUI-NOM LTD., Kibbutz Givat Brenner (IL)

(72) Inventors: Itay Zemach, Rehovot (IL); Menachem Sklarz, Beer Sheva (IL); Oswald Crasta, Lubbock, TX (US)

(73) Assignee: EQUI-NOM LTD, Kibbutz Givat Brenner (IL)

( * ) Notice: Subject to any disclaimer, the term of this patent is extended or adjusted under 35 U.S.C. 154(b) by 24 days.

This patent is subject to a terminal disclaimer.

(21) Appl. No.: 17/360,371

(22) Filed: Jun. 28, 2021

(65) Prior Publication Data

US 2022/0117187 A1    Apr. 21, 2022

Related U.S. Application Data

(63) Continuation-in-part of application No. 17/076,027, filed on Oct. 21, 2020, now Pat. No. 11,044,884.

(51) Int. Cl.
  *A01H 6/66*    (2018.01)
  *A01H 5/10*    (2018.01)

(52) U.S. Cl.
  CPC ............... *A01H 6/66* (2018.05); *A01H 5/10* (2013.01)

(58) Field of Classification Search
  None
  See application file for complete search history.

(56) References Cited

U.S. PATENT DOCUMENTS

| | | | |
|---|---|---|---|
| 4,683,202 A | 7/1987 | Mullis | |
| 5,426,039 A | 6/1995 | Wallace et al. | |
| 5,468,613 A | 11/1995 | Erlich et al. | |
| 5,492,547 A | 2/1996 | Johnson | |
| 5,565,350 A | 10/1996 | Kmiec | |
| 5,981,832 A | 11/1999 | Johnson | |
| 6,100,452 A | 8/2000 | Langham | |
| 6,455,758 B1 | 9/2002 | Johnson | |
| 6,670,524 B1 | 12/2003 | Potter et al. | |
| 7,250,552 B2 | 7/2007 | Han et al. | |
| 7,847,149 B2 | 12/2010 | Langham | |
| 8,058,503 B1 | 11/2011 | Langham | |
| 8,080,707 B2 | 12/2011 | Langham | |
| 8,581,028 B2 | 11/2013 | Langham | |
| 8,637,729 B2 | 1/2014 | Foncelle et al. | |
| 8,656,692 B2 | 2/2014 | Langham | |
| 8,664,472 B2 | 3/2014 | Langham | |
| 8,692,064 B2 | 4/2014 | Nguyen et al. | |
| 8,779,233 B1 | 7/2014 | Schnable et al. | |
| 8,987,549 B2 | 3/2015 | Baxter et al. | |
| 8,993,835 B2 | 3/2015 | Langham | |
| 9,000,258 B2 | 4/2015 | Lightart et al. | |
| 9,125,372 B1 | 9/2015 | Langham | |
| 9,144,220 B1 * | 9/2015 | Langham ................. A01H 6/66 |
| 9,167,795 B2 | 10/2015 | Langham | |
| 9,462,820 B2 | 10/2016 | Tadaki | |
| 9,485,936 B2 | 11/2016 | Page | |
| 10,577,623 B2 * | 3/2020 | Gar ........................ A01H 5/10 |
| 11,044,884 B1 * | 6/2021 | Zemach ................. C12Q 1/6895 |
| 11,395,470 B1 | 7/2022 | Zemach et al. | |
| 11,445,692 B2 * | 9/2022 | Gar ....................... C12Q 1/6895 |
| 2003/0208798 A1 | 11/2003 | Langham | |
| 2009/0235394 A1 | 9/2009 | Langham | |
| 2011/0154528 A1 | 6/2011 | Ragot et al. | |
| 2011/0271360 A1 | 11/2011 | Langham | |
| 2014/0215657 A1 | 7/2014 | Nguyen et al. | |
| 2015/0082476 A1 | 3/2015 | Baxter et al. | |
| 2015/0101073 A1 | 4/2015 | Brugmans et al. | |
| 2015/0150155 A1 | 5/2015 | Black et al. | |
| 2015/0264879 A1 | 9/2015 | Langham | |
| 2017/0055481 A1 | 3/2017 | Brugmans et al. | |
| 2018/0355368 A1 | 12/2018 | Gar et al. | |
| 2020/0093087 A1 | 3/2020 | Gar et al. | |

(Continued)

FOREIGN PATENT DOCUMENTS

| CN | 106337086 B | 6/2017 |
|---|---|---|
| IL | 239702 | 6/2015 |

(Continued)

OTHER PUBLICATIONS

Ashri A. Sesame Breeding. In: Janick J. (ed.), Plant Breeding Reviews vol. 16. John Wiley and Sons, Somerset, NJ, pp. 179-228 (1998).

Wu et al.; High-Density Genetic Map Construction and QTLs Analysis of Grain Yield-Related Traits in Sesame (*Sesamum indictim* L.) Based on RAD-Seq Technology, BMC Plant Biology 14: 274 (2014).

Office Action dated Jan. 1, 2021 for corresponding U.S. Appl. No. 17/076,027.

Notice of Allowance dated Apr. 7, 2021 for corresponding U.S. Appl. No. 17/076,027.

Wei, Wenliang et al., "Characterization of the Sesame (*Sesamum indicum* L.) Global Transcriptome Using Illumina Paired-End Sequencing and Development of EST-SSR Markers," BMC Genomics (2011) 12: 451.

Yol, Engin et al., "A High-Density SNP Genetic Map Construction Using ddRAD-Seq and Mapping of Capsule Shattering Trait in Sesame," Frontiers in Plant Science (2021) 12: 1-13.

(Continued)

*Primary Examiner* — Medina A Ibrahim

(74) *Attorney, Agent, or Firm* — Pearl Cohen Zedek Latzer Baratz LLP

(57) ABSTRACT

High yield sesame plants and parts thereof are provided. Phenotypic and genotypic analysis of many sesame varieties was performed to derive markers for phenotypic traits that contribute to high yield, and a breeding simulation was used to identify the most common and most stable markers. Examples for such phenotypic traits include the number of capsules per leaf axil, the capsule length, the height to first capsule and the number of lateral shoots. Following verification of trait stability over several generations, markers and marker cassettes were defined as being uniquely present in the developed sesame lines. The resulting high yield, shatter-resistant sesame lines can be used to increase sesame yield for its various uses.

9 Claims, 8 Drawing Sheets

Specification includes a Sequence Listing.

(56) References Cited

U.S. PATENT DOCUMENTS

| | | |
|---|---|---|
| 2021/0307285 A1 | 10/2021 | Tollman |
| 2021/0400901 A1 | 12/2021 | Tollman et al. |
| 2022/0010325 A1 | 1/2022 | Gar |

FOREIGN PATENT DOCUMENTS

| | | |
|---|---|---|
| WO | WO 93/22443 | 11/1993 |
| WO | WO 2016/067284 | 5/2016 |
| WO | WO 2017/103928 | 6/2017 |
| WO | WO 2018/211496 A1 | 11/2018 |
| WO | WO 2020/093065 | 5/2020 |
| WO | WO 2020/093065 A1 | 5/2020 |
| WO | WO 2021/202242 | 10/2021 |

OTHER PUBLICATIONS

Zhang, Haiyang et al., "Genome Sequencing of the Important Oilseed Crop *Sesamum indicum* L.," Genome Biology (2013) 14: 401.

Zhang, Haiyang et al., "Genetic Analysis and QTL Mapping of Seed Coat Color in Sesame (*Sesamum indicum* L.)," PLoS ONE, May 21, 2013, vol. 8, No. 5, pp. e63898, abstract, p. 2, col. 1, para. 2, accessed on Jan. 19, 2022 at https://journals.plos.org/plosone/article?id=10.1371/journal.pone.0063898.

GenBank JP649882 TSA (Sesamum indicum Locus_18970_Transcript_2/2_Confidence_0.8757_Length_628 mRNA sequence) Jul. 30, 2012 (retrieved Mar. 18, 2020). Retrieved from the internet <URL: https://www.ncbi.nim.nih.gov/nuccore/JP649882.1/ > whole doc.

GenBank JL343152 "TSA: Sesamum indicum cultivar Zhongzhi 11 Unigene21112 mRNA sequence") May 31, 2016 (retrieved Mar. 18, 2020). Retrieved from the internet <URL: https://www.ncbi.nim.nih.gov/nuccore/JL343152 > whole doc.

International Search Report and Written Opinion dated Apr. 6, 2020 for International Application No. PCT/US2019/059725.

International Preliminary Report on Patentability dated Apr. 27, 2021 for International Application No. PCT/US2019/059725.

Office Action dated Aug. 21, 2019 for U.S. Appl. No. 16/109,346.

Office Action dated Feb. 16, 2021 for US Application No. 16/706/752.

Notice of Allowance dated Jul. 29, 2021 for U.S. Appl. No. 16/706,752.

Office Action dated Dec. 6, 2021 in U.S. Appl. No. 16/706,752.

First Action Interview Pilot Program Pre-Interview Communication dated Dec. 21, 2021 for U.S. Appl. No. 17/474,944.

International Preliminary Report on Patentability dated Nov. 19, 2019 for PCT Application No. PCT/IL2018/050520.

European Search Report and Annex dated Mar. 18, 2022 for European Application No. 21204027.3.

Wei, Wenliang et al., "TSA: Sesamum indicum Cultivar Zhongzhi 11 Unigene2486mRNA Sequence", XP055899141, Database accession No. E_TSA:JL323849 (Oct. 2, 2011).

Zhang, Haiyang et al.; "Development and Validation of Genic-SSR Markers in Sesame by RNA-Seq." Genome Biology (2012) 13: 316.

Zhang, Haiyang et al., "TSA: Sesamum indicum Locus_1371_Transcript_1/1_Confidence_1.000_Length_2240 mRNA Sequence", XP055899043, Database accession No. EM_TSA:JP632997 (Jul. 31, 2012).

Zhou, Rong, et al. "Genome-Wide Association Studies of 39 Seed Yield-Related Traits in Sesame (*Sesamum indicum* L.)," International Journal of Molecular Sciences 19.9 (Sep. 17, 2018): 2794.

Notice of Allowance dated Feb. 28, 2022 for U.S. Appl. No. 17/474,944.

Notice of Allowability dated Apr. 11, 2022 for U.S. Appl. No. 17/474,944.

Langham et al., Progress in Mechanizing Sesame in the US Through Breeding, Reprinted from: Trends in New Crops and New Uses *Proceedings of the Fifth National Symposium*, Atlanta, Georgia, USA, Nov. 10-13, 2001, pp. 157-173. ASHS Press, 2002.

Arnheim et al., Special Report—Polymerase Chain Reaction, C&EN (1990) pp. 36-47.

Van Brunt, Amplifying Genes: PCR and its Alternatives, Bio/Technology 8:291-294 (1990).

Wu et al., Specificity of the Nick-Closing Activity of Bacteriophage T4 DNA Ligase, Gene 76:245-254 (1989).

Barringer et al., Blunt-End and Single-Strand Ligations by *Escherichia coli* Ligase: Influence on an in Vitro Amplification Scheme, Gene 89:117-122 (1990).

Sooknanan et al., NASBA—A Detection and Amplification System Uniquely Suited for RNA, Bio/Technology 13:563-564 (1995).

Cheng et al., Product Review—Long PCR, Nature 369:684-685 (1994).

Beaucage et al., Deoxynucleoside Phosphoramidites—A New Class of Key Intermediates for Deoxypolynucleotide Synthesis, Tetrahedron Letters 22(20):1859-1862 (1981).

Becker et al., Extension of the Rhizobium Meliloti Succinoglycan Biosynthesis Gene Cluster: Identification of the exsA Gene Encoding an ABC Transporter Protein, and the exsB Gene Which Probably Codes for a Regulator of Succinolycan Biosynthesis, Mol. Gen. Genet. 249:487-497 (1995).

Meksem et al., A High-Resolution Map of the Vicinity of the R1 Locus on Chromosome V of Potato Based on RFLP and AFLP Markers, Mol. Gen. Genet 249:74-81 (1995).

Jacob et al., Genetic Mapping of a Gene Causing Hypertension in the Stroke-Prone Spontaneously Hypertensive Rat. Cell 67:213-224 (1991).

Condit et al., Abundance and DNA Sequence of Two-Base Repeat Regions in Tropical Tree Genomes 34:66-71 (1991).

Girmay, A.B., Sesame Production, Challenges, and Opportunities in Ethiopia, Univ. of Aksum/Hawass Univ. (11 pgs.) (Dec. 2015).

Wang et al. "Genome sequencing ofthe high oil crop sesame provides insight into oil biosynthesis" *Genome Biology*, 15:R39, Feb. 27, 2014.

Lander ES and Botstein D. "Mapping mendelian factors underlying quantitative traits using RFLP linkage maps" Genetics. Jan. 1938;121(1):pp. 185-198.

Haley CS and Knott SA. "A simple regression method for mapping quantitative trait loci in line crosses using flanking markers" Heredity (Edinb). Oct. 1992;69(4):pp. 315-324.

Jansen, R.C. "Controlling the type I and type II errors in mapping quantitative trait loci" Genetics 138, 1994, pp. 871-881.

Kwoh et al. "Transcription-based amplification system and detection of amplified human immunodeficiency virus type 1 with a bead-based sandwich hybridization format" Proc Natl Acad Sci U S A. Feb. 1989;86(4):pp. 1173-1177.

J.C. Guatelli et al, "isothermal, in vitro amplification of nucleic acids by a multienzyme reaction modeled after retroviral replication" Proc Natl Acad Sci USA. Mar. 1990; 87(5): pp. 1874-1878.

Lomeli H. et al. "Quantitative assays based on the use of replicatabie hybridization probes" Clinical Chemistry Sep. 1989, 35 (9) pp. 1826-1831.

Landegren U. et al. "A ligase-mediated gene detection technique" Science. Aug. 26, 1988;24 1(4869):pp. 1077-1080.

Vos P. et al. "AFLP: a new technique for DNA fingerprinting" Nucleic Acids Res. Nov. 11, 1995;23(21):pp. 4407-4414.

Lincoln, S., Daiy, M. & Lander, E.S, "Mapping genes controlling quantitative traits with MAPMAKER/QTL 1.1." in Whitehead Institute Technical Report vol. 2, Whitehead Institute, Cambridge, Massachusetts, 1994.

Yefim Ronin et al. "Building reliable genetic maps: different mapping strategies may result in different maps" Natural Science, vol. 2, Issue 6, Jan. 2010, pp. 576-589.

Korol A.B. et al. "Enhanced efficiency of quantitative trait loci mapping analysis based on multivariate complexes of quantitative traits" Genetics. Apr. 2001; 157(4): pp. 1789-1803.

L Kruglyak and E S Lander "A nonparametric approach for mapping quantitative trait loci" Genetics Mar. 1, 1995 vol. 139 No. 3, pp. 1421-1428.

Jansen RC and Stam P. "High resolution of quantitative traits into multiple loci via interval mapping" Genetics. Apr. 1994;136(4):pp. 1447-1455.

(56) References Cited

OTHER PUBLICATIONS

Zeng ZB "Precision mapping of quantitative trait loci" Genetics.;136(4), Apr. 1994; pp. 1457-1468.
Utz and Melchinger "Biometrics in Plant Breeding", van Oijen, Jansen (eds.) Proceedings of the Ninth Meeting of the Eucarpia Section Biometrics in Plant Breeding, The Netherlands, 1994, pp. 195-204.
R.S. Reiter et al. "Global and local genome mapping in *Arabidopsis thaliana* by using recombinant inbred lines and random amplified polymorphic DNAs" Proc Natl Acad Sci U S A., Feb. 15, 1992; 89(4): pp. 1477-1481.
Ashri A. & Singh R.J "Chromosome Engineering and Crop Improvement" Sesame (*Seamum indicum* L.) Genetic Resources Oilseed Crops, 4, 2007, pp. 231-280.
Singh et al. "Unlocking the Potential of Genetic Resources for Improvement of Sesame (*Sesamum indicum* L.): The Current Scenario" Gene Pool Diversity and Crop improvement: vol. 1, Chapter 15, Feb. 2016, pp. 447-479.
Wang et al. "Updated sesame genome assembly and fine mapping of plant height, and seed coat color QTLs using a new high-density genetic map" BMC Genomics. 5;17:31, Jan. 2016.
International Search Report for PCT Application No. PCT/IL2016/050520, dated Jul. 22, 2018.
Notice of Allowance dated Oct. 17, 2019 for related U.S. Appl. No. 16/109,346, U.S. Pat. No. 10,577,623, issued Mar. 3, 2020.
Dan Migafarov: An alternative to GMOs: how to design plants without interfering with the genome; Sep. 14, 2016, retrieved from the Internet: https://agravery.com/uk/posts/show/alternative-gmo-ak-mozna-konstruuvati-roslini-ne-vtrucaucis-v-genom.
Uzin B et al; Identificationof a molecular marker linked to the closed capsule mutant trait in sesame using AFLP; Plant Breeding, Paul Parey Scientific Publ, Berlin, DE, vol. 122, No. 1, Feb. 1, 2003, pp. 95-97.
Search Report dated Nov. 24, 2020 for related European Application No. EP18802371 .7.
Zhang et al: Construction of a high-density genetic map for sesame based on large scale marker development by specific length amplified fragment (SLAF) sequencing; BMC Plant Biology, 2013, 13:141.
Office Action dated Apr. 4, 2019 for related U.S. Appl. No. 16/109,346.
Notice before Acceptance dated Nov. 22, 2022 for co-pending Israeli Application No. 287415 (corresponding to U.S. Appl. No. 17/360,371).
Notice of Allowance dated May 11, 2022 for U.S. Appl. No. 16/706,752.
Notice before Acceptance dated Nov. 29, 2022 for Israeli Application No. 270585 (corresponding to PCT Application No. PCT/IL2018/050520 and U.S. Appl. No. 16/109,346).
International Preliminary Report on Patentability dated Sep. 29, 2022 for PCT International Application No. PCT/US2021/024190.
International Search Report, Search Strategy, and Written Opinion dated Sep. 9, 2021 for PCT International Application No. PCT/US2021/024190.
U.S. Department of Agriculture Plant Variety Protection Certificate re PVP Application No. 201900246, Variety Name ES103, dated Jun. 22, 2020.
U.S. Department of Agriculture Plant Variety Protection Certificate re PVP Application No. 201900247, Variety Name ES107, dated Jun. 22, 2020.
U.S. Department of Agriculture Plant Variety Protection Certificate re PVP Application No. 201900248, Variety Name ES108, dated Jun. 22, 2020.

\* cited by examiner

SEQUENCE LISTING

<160> NUMBER OF SEQ ID NOS: 14

<210> SEQ ID NO 1
<211> LENGTH: 160
<212> TYPE: DNA
<213> ORGANISM: Sesamum indicum

<400> SEQUENCE: 1

```
ctatctttgt gataatccta taaattaaac aaaaatacca ttgactattg agattagaga      60
aagatgcaat ttaactcatc taatatgaga aatgagtaaa agtgttatga taatttgcta     120
attccttttt tgcactggtt tatctgctca tttcacatat                            160
```

<210> SEQ ID NO 2
<211> LENGTH: 160
<212> TYPE: DNA
<213> ORGANISM: Sesamum indicum -continued

```
<400> SEQUENCE: 2
ctatctttgt gataatccta taaattaaac aaaaatacca ttgactattg agattagaga      60
aagatgcaat ttaactcatg taatatgaga aatgagtaaa agtgttatga taatttgcta     120 attcctttt tgcactggtt tatctgctca tttcacatat                            160

<210> SEQ ID NO 3
<211> LENGTH: 201
<212> TYPE: DNA
<213> ORGANISM: Sesamum indicum

<400> SEQUENCE: 3 agttttgtt cttaaacagt gcattttttt tttttttgac aaaattcatt attttcatta      60
tcttgctgtc aaatataatg aaaaaattca tctgaggctg ttttgagggt gggaaagaaa    120
aactatcatt tcctccctga aatttaattt tttgaatatt taatcatatt cggacaggtg   180
atattttcac ataaaagcaa t                                              201

<210> SEQ ID NO 4
<211> LENGTH: 201
<212> TYPE: DNA
<213> ORGANISM: Sesamum indicum

<400> SEQUENCE: 4 agttttgtt cttaaacagt gcattttttt tttttttgac aaaattcatt attttcatta      60
tcttgctgtc aaatataatg aaaaaattca tctgaggctg ctttgagggt gggaaagaaa    120
aactatcatt tcctccctga aatttaattt tttgaatatt taatcatatt cggacaggtg   180
atattttcac ataaaagcaa t                                              201

<210> SEQ ID NO 5
<211> LENGTH: 201
<212> TYPE: DNA
<213> ORGANISM: Sesamum indicum

<400> SEQUENCE: 5
aacacaaaaa accaaacact ttcatatgat catagttagg ggccttctta tataataatt     60
catagggtgt tttccaactt aatgtttgtg ttggaagtct attaattatg tatgtggcag    120
ctaacaatgc ctcggcccag aatctttgtg gcatgtttgc ttggaacatc aaagatctag   180
ccccttgaaa aaggtgttgg t                                              201

<210> SEQ ID NO 6
<211> LENGTH: 201
<212> TYPE: DNA
<213> ORGANISM: Sesamum indicum

<400> SEQUENCE: 6
aacacaaaaa accaaacact ttcatatgat catagttagg ggccttctta tataataatt     60
catagggtgt tttccaactt aatgtttgtg ttggaagtct gttaattatg tatgtggcag    120
ctaacaatgc ctcggcccag aatctttgtg gcatgtttgc ttggaacatc aaagatctag   180
ccccttgaaa aaggtgttgg t                                              201

<210> SEQ ID NO 7
<211> LENGTH: 160
<212> TYPE: DNA
<213> ORGANISM: Sesamum indicum
```

<400> SEQUENCE: 7

```
atttggagcc gggttcacat tgtttccagc ctctcaaagg attttggtct tccaggattc    60
aggatcggca tgatctattt caacagtaaa accctgattg ctgctgcaac aaaaatgtcg   120
agttttgggc tggtctcttc tcaatcccag ttcctactgt                         160
```

<210> SEQ ID NO 8
<211> LENGTH: 160
<212> TYPE: DNA
<213> ORGANISM: Sesamum indicum

<400> SEQUENCE: 8

```
atttggagcc gggttcacat tgtttccagc ctctcaaagg attttggtct tccaggattc    60
aggatcggca tgatctattc caacagtaaa accctgattg ctgctgcaac aaaaatgtcg   120
agttttgggc tggtctcttc tcaatcccag ttcctactgt                         160
```

<210> SEQ ID NO 9
<211> LENGTH: 198
<212> TYPE: DNA
<213> ORGANISM: Sesamum indicum

<400> SEQUENCE: 9

```
ttaaagtgat gagagttgat gttactgaga atataaatga ggatactgtg aagcagttta    60
tcgaagaaga caatgagaac acaaccagca aggacaccaa agaggaagtt actgatatgg   120
gtaacaatca gccagatcga gttgctgcac aaggagataa tgatgtgatg aagatgaaa   180
ataatttaga catgaagc                                                 198
```

<210> SEQ ID NO 10
<211> LENGTH: 198
<212> TYPE: DNA
<213> ORGANISM: Sesamum indicum

<400> SEQUENCE: 10

```
ttaaagtgat gagagttgat gttactgaga atataaatga ggatactgtg aagcagttta    60
tcgaagaaga caatgagaac acaaccagca aggacaccga agaggaagtt actgatatgg   120
gtaacaatca gccagatcga gttgctgcac aaggagataa tgatgtgatg aagatgaaa   180
ataatttaga catgaagc                                                 198
```

<210> SEQ ID NO 11
<211> LENGTH: 201
<212> TYPE: DNA
<213> ORGANISM: Sesamum indicum

<400> SEQUENCE: 11

```
atcatgaatt ttactcctat ttttttgtta atattaacaa atctagtgga ttttgactaa    60
caaagggact tattttatta aacgaaagca accttcaagg atattaaata taattttca   120
aaccacatga gatttatatg caattacatt aaatttcggt agagtggagt agttatccct   180
agaaatatta cagtcgaagt g                                             201
```

<210> SEQ ID NO 12
<211> LENGTH: 201
<212> TYPE: DNA
<213> ORGANISM: Sesamum indicum

<400> SEQUENCE: 12

```
atcatgaatt ttactcctat ttttttgtta atattaacaa atctagtgga ttttgactaa    60
```

```
caaagggact tatttatta aacgaaagca accttcaagg gtattaaata taattttca      120 aaccacatga gatttatatg caattacatt aaatttcggt agagtggagt agttatccct    180
agaaatatta cagtcgaagt g                                              201

<210> SEQ ID NO 13
<211> LENGTH: 301
<212> TYPE: DNA
<213> ORGANISM: Sesamum indicum

<400> SEQUENCE: 13
ggaggcaaaa gaatacgggt tggttgatgc agtgatcgat gatggcaagc ctggactagt     60
cgcacccatc gcagatactg caccccacc aaaaacccgt gtctgggatc tttggaaaat    120
cgaaggcagt aaaaaagcca agaaaaactt accctccgaa gagaaactat tacaaaatgg   180
atacacagtt ggccaaggtg aagatgacag aagcacggaa caggtagagg aagcaccaac   240
atctcaatga gtaatgaatg ttgagatatt tcttgtatac actgtcaaac attgtagcta   300
g                                                                    301

<210> SEQ ID NO 14
<211> LENGTH: 301
<212> TYPE: DNA
<213> ORGANISM: Sesamum indicum

<400> SEQUENCE: 14
ggaggcaaaa gaatacgggt tggttgatgc agtgatcgat gatggcaagc ctggactagt     60
cgcacccatc gcagatactg caccccacc aaaaacccgt gtctgggatc tttggaaaat    120
cgaaggcagt aaaaaagcca agaaaaactt gccctccgaa gagaaactat tacaaaatgg   180
atacacagtt ggccaaggtg aagatgacag aagcacggaa caggtagagg aagcaccaac   240
atctcaatga gtaatgaatg ttgagatatt tcttgtatac actgtcaaac attgtagcta   300
g                                                                    301
```

HIGH YIELD SESAME

CROSS REFERENCE TO RELATED APPLICATIONS

This application is a continuation in part of U.S. application Ser. No. 17/076,027, filed on Oct. 21, 2020, which is incorporated herein by reference in its entirety.

SEQUENCE LISTING INCORPORATION

The ".txt" Sequence Listing filed with this application by EFS and which is entitled P-597354-US1-SQL-27JUN21.txt, is 5.49 kilobytes in size and which was created on Jun. 27, 2021, is hereby incorporated by reference.

BACKGROUND OF THE INVENTION

1. Technical Field

The present invention relates to the field of sesame genetics and breeding, and more particularly, to quantitative trait loci (QTLs, or QTL) associated with sesame crop yield.

2. Discussion of Related Art

Sesame (*Sesamum indicum*) is an oilseed crop that is cultivated over a large range of soil and climate conditions, typically in subtropical climates, and is used for seeds, oil and paste products. Low yield varieties are commonly used, yet such varieties make sesame non-profitable to grow in developed countries.

Certificates under the U.S. Plant Variety Protection Act regarding PV Accession Nos. 201900246, 201900247 and 201900248 have been issued for seed varieties "ES103", ES107", and "ES108", respectively, and deposits of at least 3,000 seeds of each of the varieties were submitted on Jul. 30, 2019 to the National Laboratory for Genetic Resources Preservation, 1111 S Mason St, Fort Collins, Colo. 80521-4500, United States, a public depositary, under the PVPA.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides high yield sesame plants with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NOs: 7 or 8, wherein the sesame plant or part thereof is homozygous with respect to SEQ ID NO: 7 or heterozygous at QTL 4, and wherein the sesame plant further comprises QTLs 1, 2, 3 and/or QTLs 5, 6, 7.

Other features and advantages of this invention will become apparent from the following detailed description, examples, and figures. It should be understood, however, that the detailed description and the specific examples while indicating preferred embodiments are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1 is a high-level schematic illustration of sesame chromosomes with indications of the relevant QTL markers, according to some embodiments of the invention.

Figure 2A:
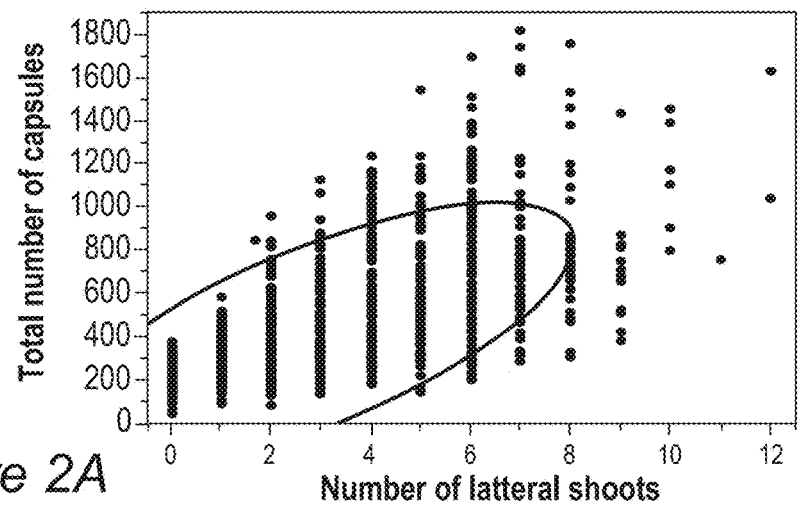
Figure 2B:
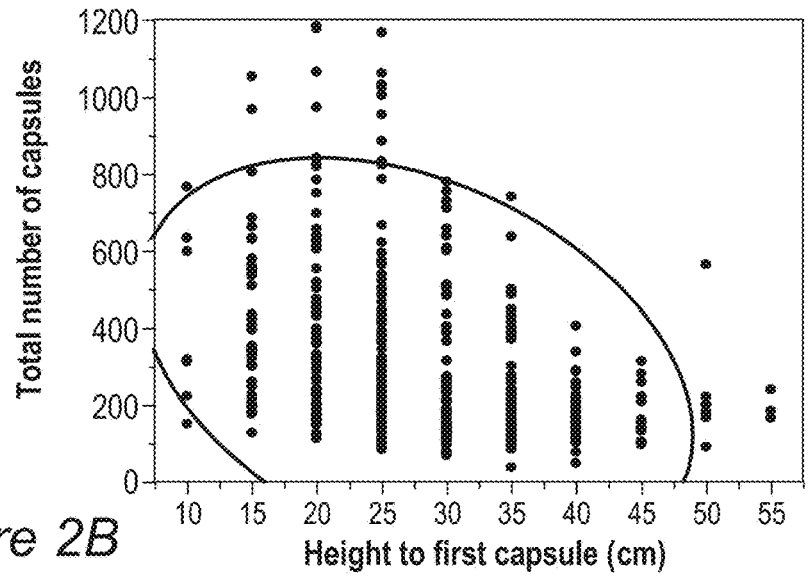
Figure 2C:
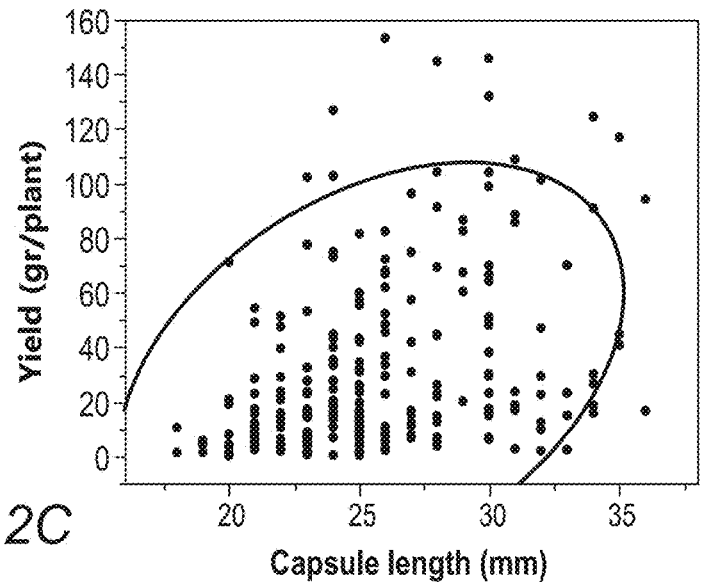

FIGS. 2A-2C present experimental results indicating the correlation between phenotypic traits and the higher yield in sesame varieties with the disclosed marker cassettes, according to some embodiments of the invention.

Figure 3A:
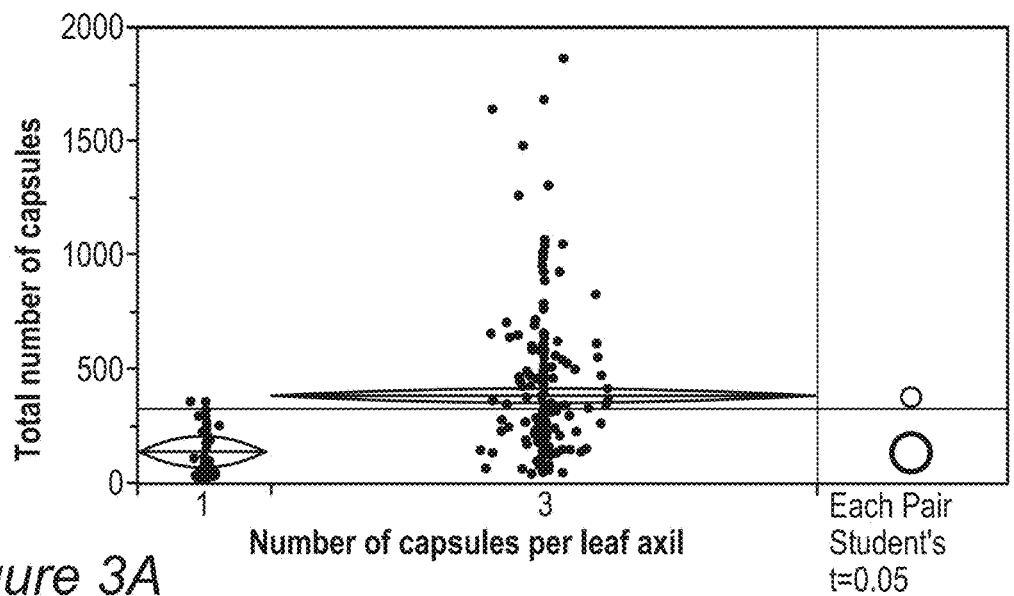
Figure 3B:
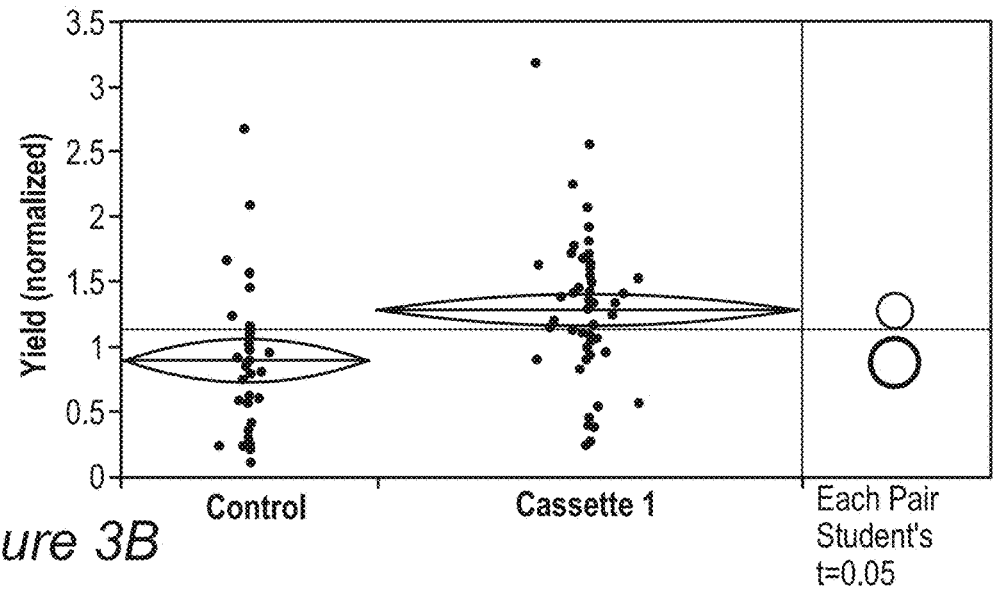
Figure 3C:
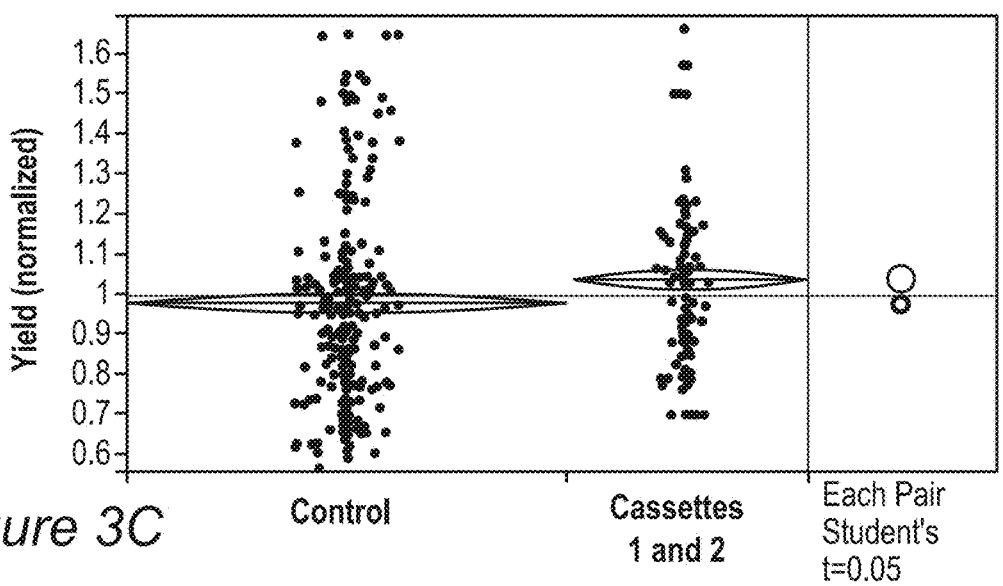

FIGS. 3A-3C present experimental results indicating the significant differences provided by the disclosed cassettes on overall yield in sesame, according to some embodiments of the invention.

Figure 4:
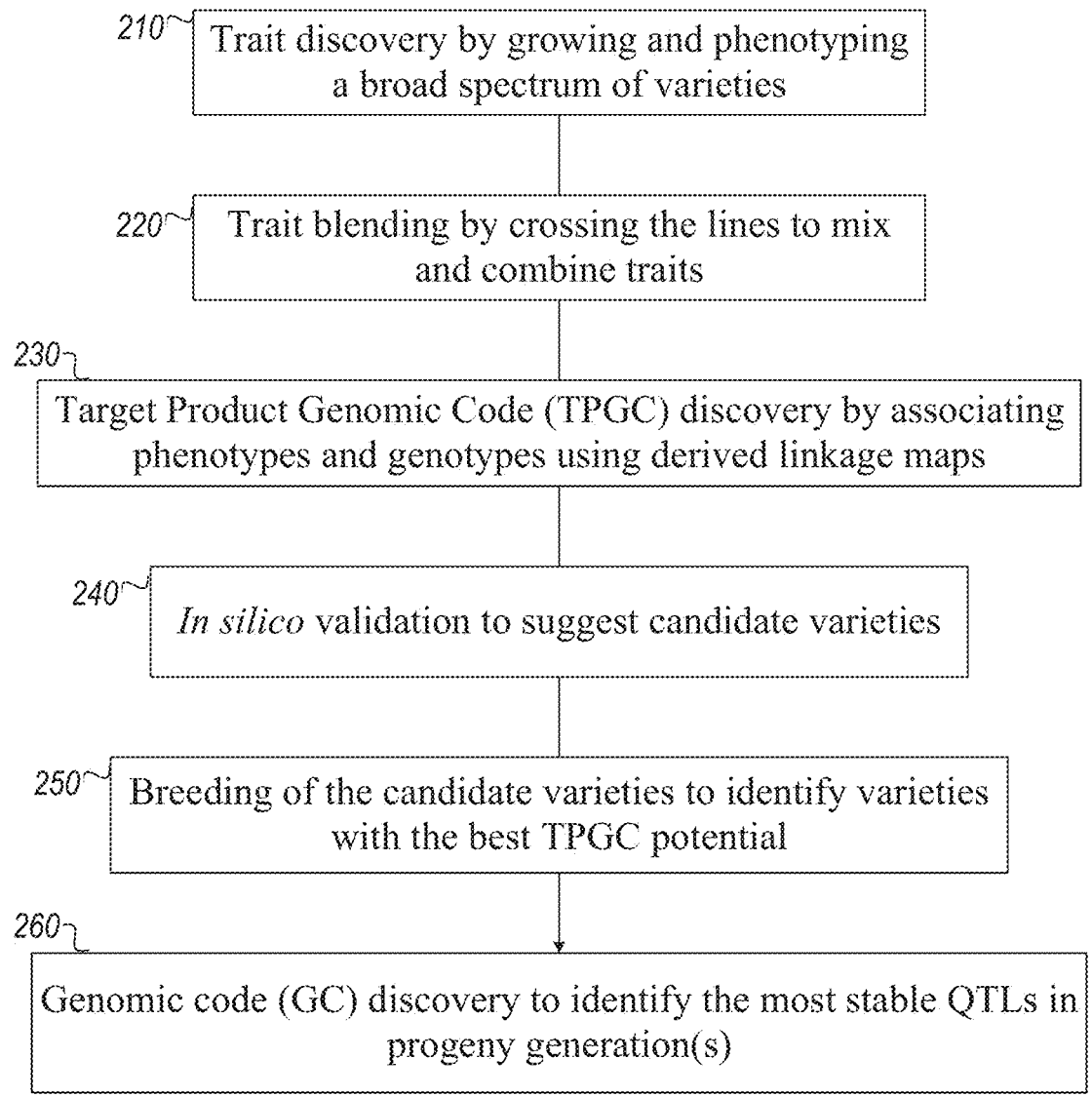

FIG. 4 is a high-level schematic illustration of a computationally supported breeding method, according to some embodiments of the invention.

Figure 5A:
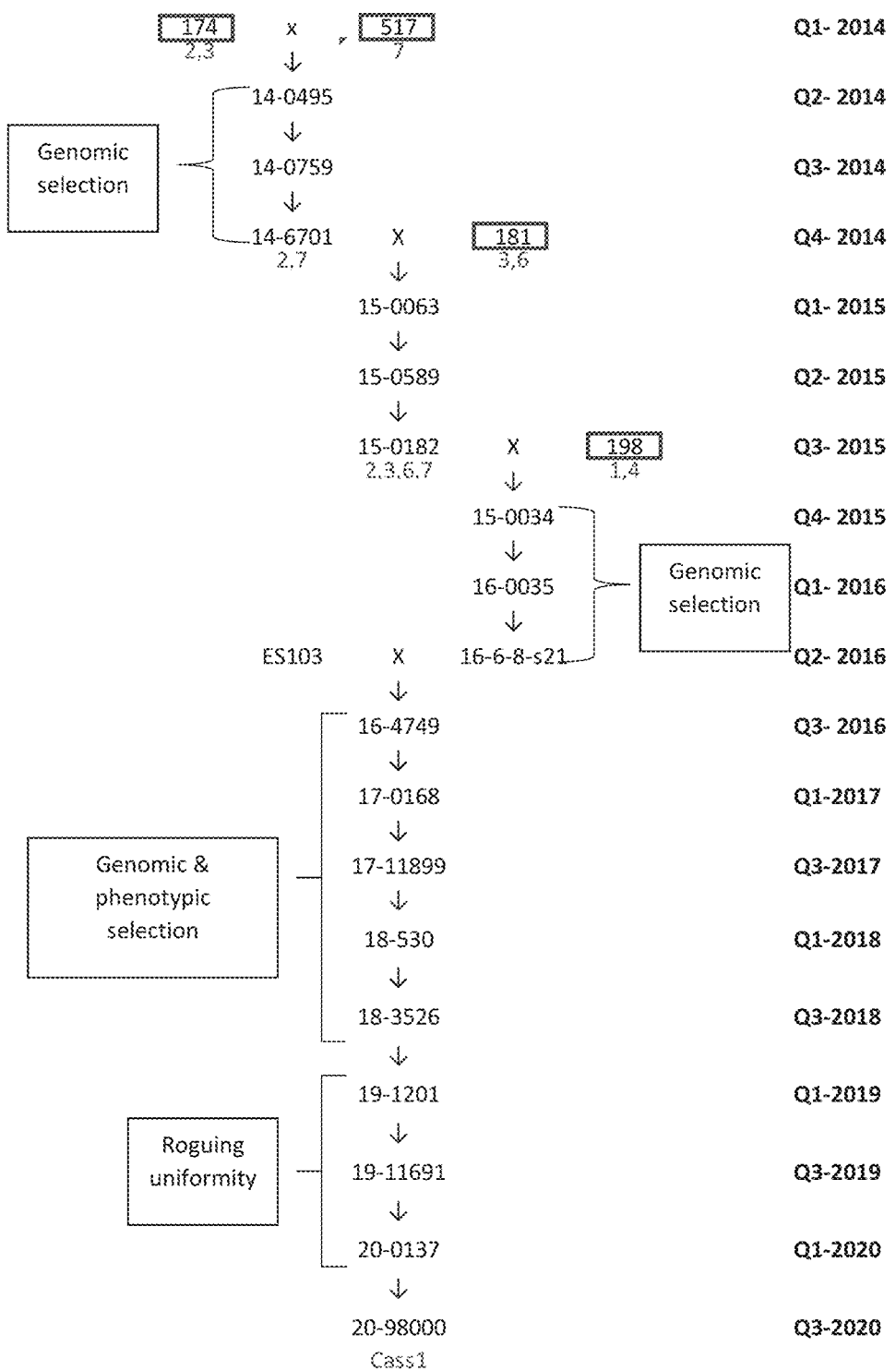
Figure 5B:
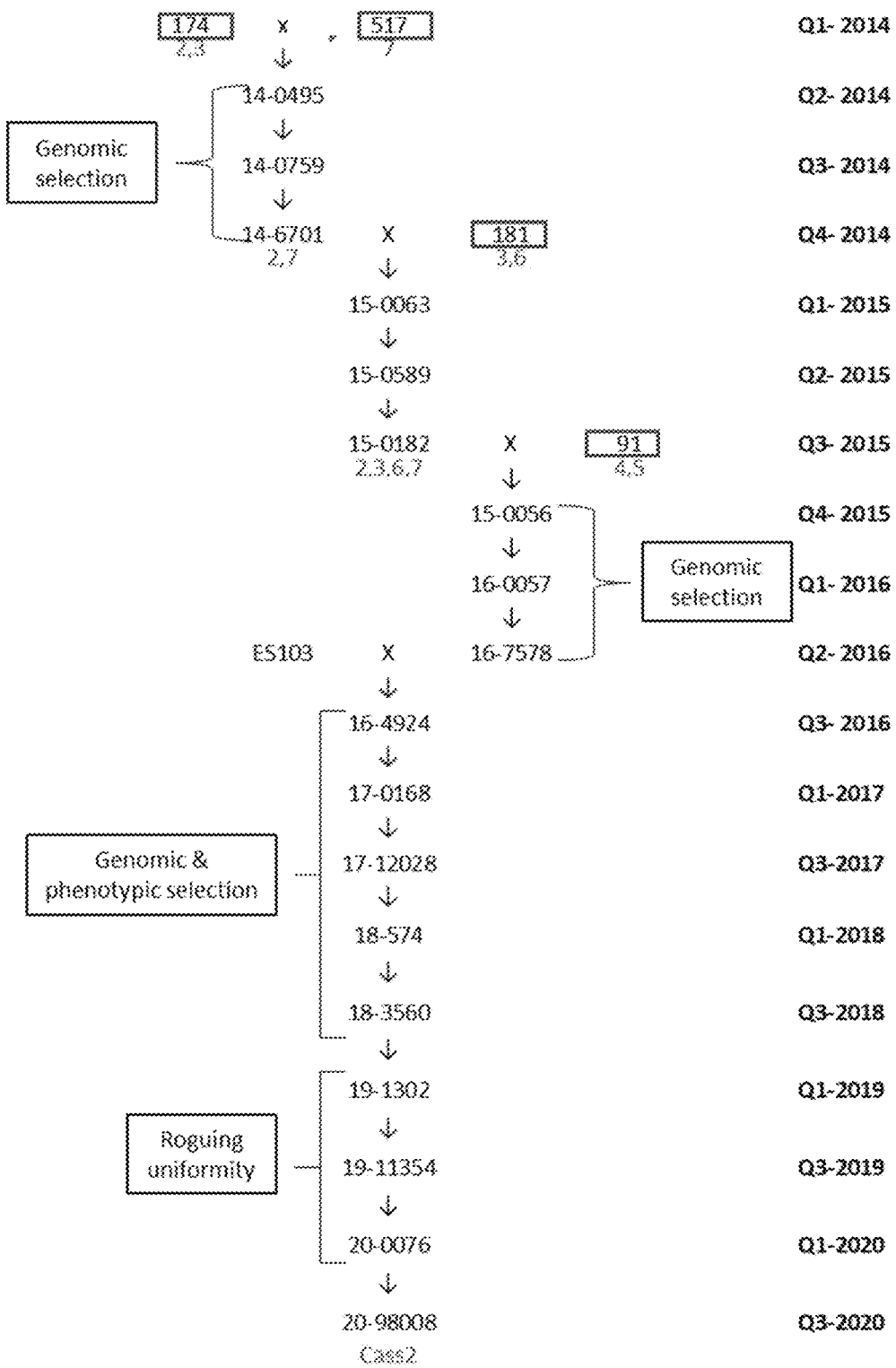
Figure 5C:
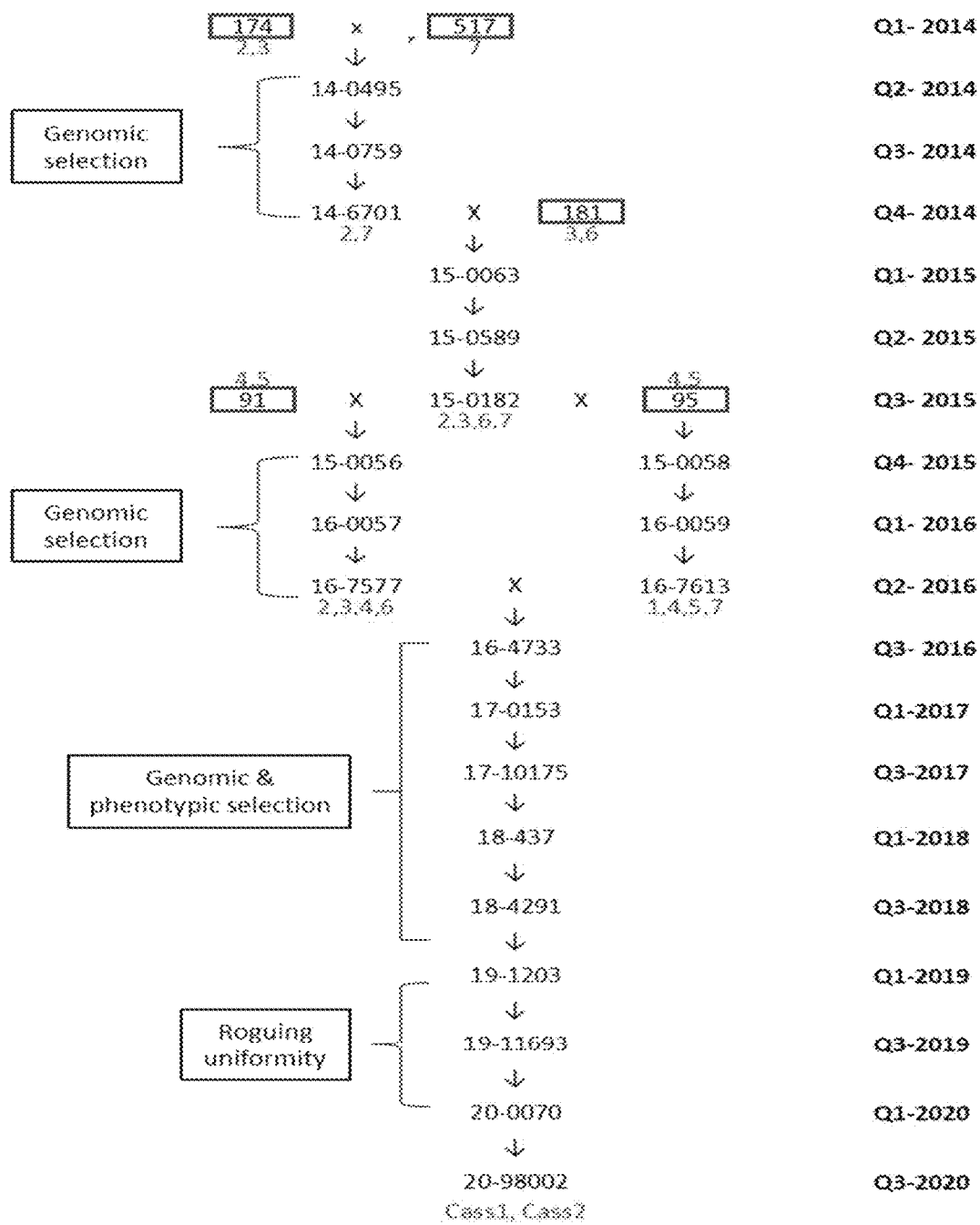

FIGS. 5A-5C provide non-limiting examples for disclosed high yield sesame plants with shatter-resistant capsules that were bred with computational support and comprise disclosed QTLs, according to some embodiments of the invention.

Figure 6C:
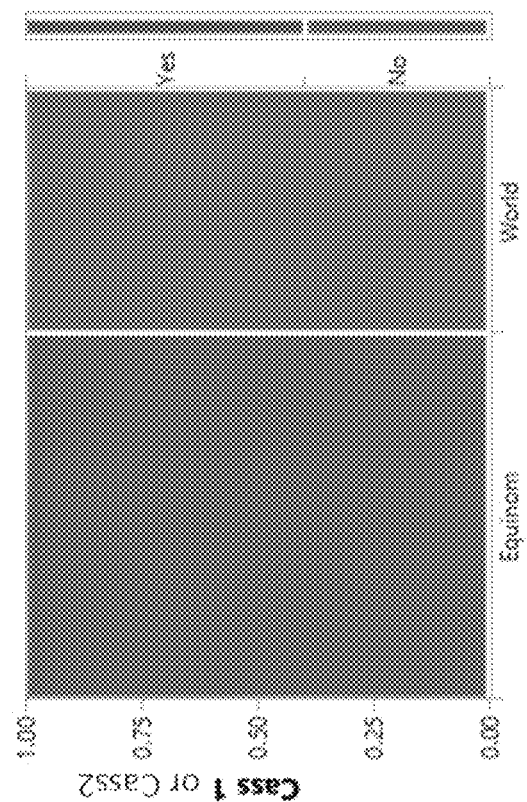
Figure 6A:
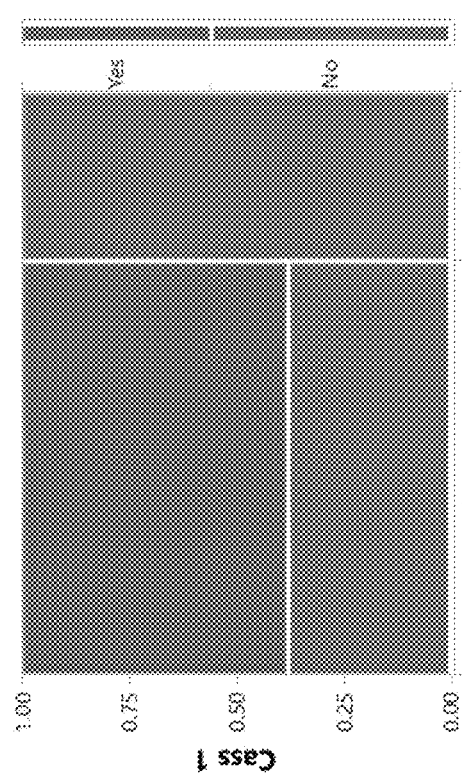
Figure 6B:
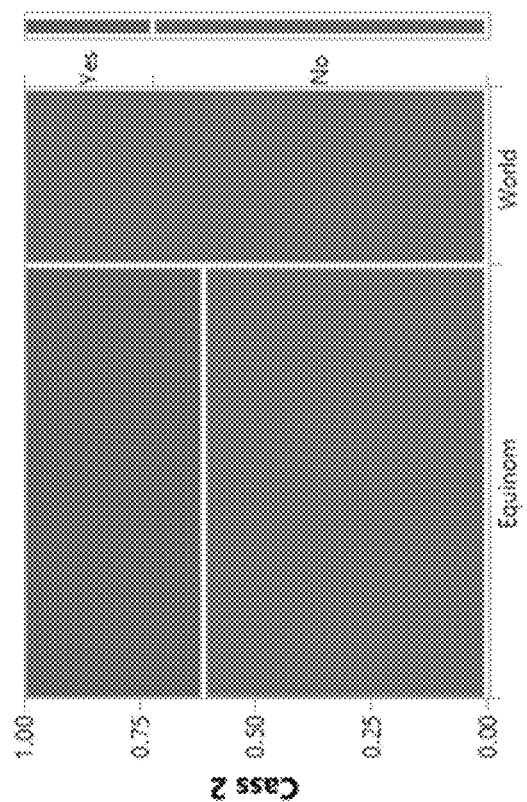

FIGS. 6A-6C provide a comparison of 514 high yield shatter-resistant sesame plant varieties, according to some embodiments of the invention, with 210 world varieties.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the terminology employed herein are for the purpose of description and should not be regarded as limiting.

Sesame plants and parts thereof are provided, which provide higher yield than current varieties. Phenotypic and genotypic analyses of many sesame varieties were performed to derive markers for high yield and other yield related phenotypic traits, and a breeding simulation was used to identify the most common and most stable markers. Following verification of trait stability over several generations, markers and marker cassettes were defined as being uniquely present in the developed sesame lines. The resulting high yield sesame lines can be used to increase the yield of sesame crops for their various uses.

U.S. Pat. No. 10,577,623 and U.S. Patent Application Publication No. 2020/0093087 teach QTLs that confer shatter resistant capsules, and elite sesame varieties having shatter resistant capsules. Shatter resistant lines were used at least partly to further derive the disclosed high yield sesame lines disclosed herein.

In one aspect, this invention provides a high yield sesame plant with shatter-resistant capsules, progeny thereof and/or part(s) thereof, the sesame plant comprises: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7, wherein the QTLs and markers associated with the Capsule length trait comprise QTLs 1, 2, and 3 with corresponding markers set forth in SEQ ID NO: 1. SEQ ID NO: 3, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In an embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5, and the sesame plant is homozygous with respect to SEQ ID NO: 5. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In some embodiments of the sesame plant, progeny thereof and/or part(s) thereof, the phenotypic traits comprise a high yield of at least ten percent more than control sesame lines ES103. ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprises: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7, and wherein the QTLs and markers associated with the Capsule length trait comprise QTLs 1, 2, and 3 with corresponding markers set forth in SEQ ID NO: 1, SEQ ID NO: 3, and SEQ ID NO: 6. In an embodiment of the high yield sesame plant, progeny thereof and/or part(s), the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof 10, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103. ES107 and ES108. In another embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprises: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7 and SEQ ID NO: 8, wherein the sesame plant or part thereof is heterozygous at QTL 4, and wherein the QTLs and markers associated with the Capsule length trait comprise QTLs 1, 2, and 3 with corresponding markers set forth in SEQ ID NO: 1, SEQ ID NO: 3, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1, and SEQ ID NO: 5, the sesame plant or part thereof is homozygous with respect to SEQ ID NO: 1 or heterozygous at QTL 3, the sesame plant or part thereof is homozygous with respect to SEQ ID NO: 3 or is heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103. ES107 and ES108. The sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprises: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7 and SEQ ID NO: 8, wherein the sesame plant or part thereof is heterozygous at QTL 4, and wherein the QTLs and markers associated with the Capsule length trait comprise QTLs 1, 2, and 3 with corresponding markers set forth in SEQ ID NO: 1, SEQ ID NO: 3, and SEQ ID NO: 6. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In an embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In another embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103, ES107 and ES108. In another embodiment of The sesame plant, progeny thereof and/or part(s) thereof, the part(s) comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 1, SEQ ID NO: 4, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In an embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In another embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103. ES107 and ES108. In another embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 1, SEQ ID NO: 4, and SEQ ID NO: 6. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait In one aspect, this invention provides a high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 3, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 4, and SEQ ID NO: 6. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 4, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In another embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 7, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 4, and SEQ ID NO: 6. In an embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In an embodiment of the sesame plant, progeny thereof and/or part(s) thereof, the phenotypic traits comprise a high yield of at least ten percent more than control sesame lines ES103. ES107 and ES108. In another embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 1, SEQ ID NO: 4, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103. ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 1, SEQ ID NO: 4, and SEQ ID NO: 6.

In an embodiment of the high yield sesame plant, progeny thereof and/or part(s), the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13; or heterozygous at QTL 7. In another embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 3, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 3, and SEQ ID NO: 6.

In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, wherein the pan(s) thereof comprise any of a seed, an endosperm, an ovule, pollen, cell, cell culture, tissue culture, plant organ, protoplast, meristem, embryo, or a combination thereof.

In another aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 4, and SEQ ID NO: 5. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10. SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103. ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

In one aspect, this invention provides a high yield sesame plant with shatter-resistant capsules, progeny thereof and/or part(s) thereof, the sesame plant comprising a plurality of quantitative trait loci (QTLs) having a corresponding plurality of nucleic acid genetic markers that are associated with a plurality of phenotypic traits of the sesame plant, wherein the QTLs are combined in the sesame plant from a plurality of sesame varieties by computationally supported breeding, wherein the phenotypic traits comprise at least a Number of capsules per leaf axil trait, a Capsule length trait, a Number of lateral shoots trait and a Height to first capsule trait, wherein the QTL and marker associated with the Number of capsules per leaf axil trait comprise QTL 4 with corresponding markers set forth in SEQ ID NO: 8, wherein the sesame plant or part thereof is homozygous with respect to SEQ ID NO: 7 or heterozygous at QTL 4, and wherein the QTLs and markers associated with the Capsule length trait comprise QTLs 1, 2, and 3 with corresponding markers set forth in SEQ ID NO: 2; SEQ ID NO: 4, and SEQ ID NO: 6. In an embodiment of the high yield sesame plant, progeny thereof and/or part(s) thereof, the QTLs and markers associated with the Height to first capsule trait comprise QTLs 1 and 3 with corresponding markers set forth in one of: SEQ ID NO: 1 and SEQ ID NO: 5, the sesame plant or part thereof is homozygous with respect to SEQ ID NO: 1 or heterozygous at QTL 1, the sesame plant or part thereof is homozygous with respect to SEQ ID NO: 3 or heterozygous at QTL 2, and the sesame plant or part thereof is homozygous with respect to SEQ ID NO: 5 or heterozygous at QTL 3. In another embodiment of the high yield sesame plant, progeny thereof and/or part(s) thereof, the phenotypic traits further comprise a Number of lateral shoots trait, the QTL and marker associated with the Number of capsules per leaf axil trait comprise QTL 3 with corresponding markers set forth in SEQ ID NOs: 5 or 6, and the sesame plant is homozygous with respect to SEQ ID NO: 5 or heterozygous at QTL 3. In an embodiment of the high yield sesame plant, progeny thereof and/or part(s) thereof, the QTLs and markers associated with the Capsule length trait, the Height to first capsule trait and the Number of lateral shoots trait comprise QTLs 5, 6, 7 with corresponding markers set forth in SEQ ID NOs: 9 or 10, SEQ ID NOs: 11 or 12, and SEQ ID NOs: 13 or 14, respectively, the sesame plant is homozygous with respect to SEQ ID NO: 9 or heterozygous at QTL 5, the sesame plant is homozygous with respect to SEQ ID NO: 11 or heterozygous at QTL 6, and the sesame plant is homozygous with respect to SEQ ID NO: 13: or heterozygous at QTL 7. In another embodiment of the sesame plant, progeny thereof and/or part(s) thereof, the phenotypic traits comprise a high yield of at least ten percent more than control sesame lines ES103, ES107 and ES108. In an embodiment of the sesame plant, progeny thereof and/or part(s) thereof, the part(s) thereof comprise any of a seed, an endosperm, an ovule, pollen, cell, cell culture, tissue culture, plant organ, protoplast, meristem, embryo, or a combination thereof.

Shatter resistant capsules were characterized in fully developed capsules having at most 10% seed moisture, and the shatter-resistant capsules were characterized by at least one of the features: (i) at least 80% seed retention after shaking the plant, (ii) at least 80% seed retention after the capsules are turned upside down, (iii) a ratio of at least 5:1 between a total length of the capsule and a length of a zone in which the capsule tips are open, and/or 20-30% of the capsules retain 90-95% of the seeds in fully developed green capsules before drying.

Various embodiments comprise high yield sesame plants with shatter-resistant capsules, or part(s) thereof, that comprise a plurality of loci associated with a corresponding plurality of quantitative trait loci (QTLs) having a corresponding plurality of nucleic acid genetic markers that are associated with a plurality of phenotypic traits of the sesame plant. The QTLs are combined in the sesame plants from a plurality of sesame varieties according to computationally supported breeding tools. Phenotypic and genotypic analyses of many sesame varieties were performed to derive markers for phenotypic traits that contribute to high yield, and a breeding simulation was used to identify the most common and most stable markers. Examples for such phenotypic traits include the number of capsules per leaf axil (e.g., 1 or 3), the capsule length (e.g., 15-37 mm), the height (on the plant stem) to the first capsule (e.g., 10-55 cm) and the number of lateral shoots (e.g., 0 to 12). Following verification of trait stability over several generations, markers and marker cassettes were defined as being uniquely present in the developed sesame lines. The resulting high yield sesame lines can be used to increase sesame yield for its various uses. Details concerning the QTLs and markers are provided in Table 1 below, and the methods used to develop and select the varieties are disclosed with respect to FIG. 4 below.

It is noted that disclosed high yield sesame plants with shatter-resistant capsules are hybridized in that none of the disclosed varieties occurs in nature or in known worldwide sesame varieties. The high yield sesame plants with shatter-resistant capsules are characterized by the disclosed QTL markers which were judiciously detected in other varieties, selected and gradually introduced in the disclosed combinations to yield the disclosed high yield sesame plants with shatter-resistant capsules. Once specific disclosed high yield sesame plants with shatter-resistant capsules were achieved, further breeding was used to stabilize the varieties and assure constant phenotypes for sesame production, making the varieties pure lines. The term "hybridized" is used herein to define disclosed varieties having QTL markers and traits collected during the breeding process from different varieties that were determined and hybridized during the highly complicated computationally-supported breeding methods described below, in which the genotypes of multiple sesame varieties have been judiciously combined and analyzed, to discover and accumulate the recited QTL markers and corresponding phenotypical traits into the disclosed high yield sesame plant with shatter-resistant capsules. Although the recited sesame plants are not genetically modified by sequences originating from other species, they cannot be reached merely by natural processes, as is evident by the detailed and intentional breeding program that was applied to specifically measure required characteristics, detect corresponding markers using bioinformatics methods and combine the detected QTLs in the selected varieties by classic breeding approaches (e.g., hand pollination crosses and single plant selections). For example, any further generation derived from the disclosed high yield sesame plants with shatter-resistant capsules is also understood to be a high yield sesame plant with shatter-resistant capsules.

Figure 1:
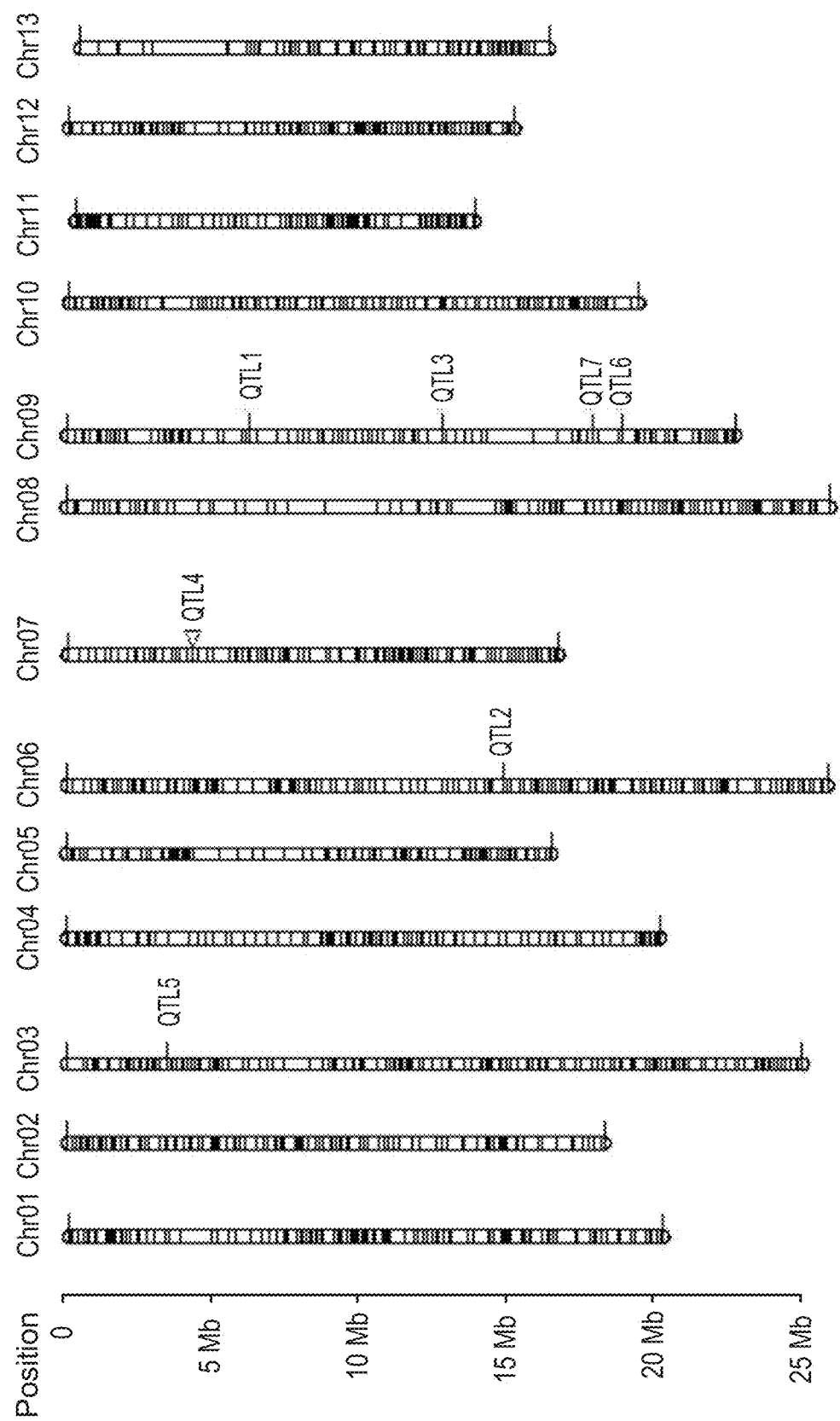

FIG. 1 is a high-level schematic illustration of sesame chromosomes with indications of the relevant QTL markers, according to some embodiments of the invention. FIG. 1 illustrates schematically the thirteen sesame chromosomes and the marker locations indicated along them.

Table 1 provides the derived genetic markers, QTLs, corresponding traits and resulting marker cassettes, according to some embodiments of the invention.

TABLE 1

Genetic markers, QTLs, corresponding traits and marker cassettes with corresponding high yield components.

| QTL | SEQ ID NO | MarkerID | Chromosome, Position, Strand [1] | QTL P-value | Phenotypic trait |
|---|---|---|---|---|---|
| 1 | 1, 2 | MaSI0003637 | Chr9, 6319255, + | <0.05 | Capsule length<br>Height to first capsule |
| 2 | 3, 4 | MaSI0003889 | Chr6, 14822546, + | <0.05 | Capsule length |
| 3 | 5, 6 | MaSI0003835 | Chr9, 12880820, + | <0.05 | Capsule length<br>Height to first capsule<br>Number of lateral shoots |
| 4 | 7, 8 | MaSI0003448 | Chr7, 4339429, + | <0.05 | Number of capsules per leaf axil |
| 5 | 9, 10 | MaSI0003358 | Chr3, 3895479, + | <0.05 | Capsule length<br>Height to first capsule |
| 6 | 11, 12 | MaSI0003838 | Chr9, 18953887, + | <0.05 | Capsule length<br>Height to first capsule |
| 7 | 13, 14 | MaSI0003635 | Chr9, 17947299, − | <0.05 | Number of lateral shoots |

| QTL | SEQ ID NO | Allele 1 | Allele 2 | Cassette (with respective QTLs) 1 | Cassette (with respective QTLs) 2 |
|---|---|---|---|---|---|
| 1 | 1, 2 | C | G | CC/CG | |
| 2 | 3, 4 | T | C | TT/TC | |
| 3 | 5, 6 | A | G | AA/AG | |
| 4 | 7, 8 | T | C | TT/TC | TT/TC |
| 5 | 9, 10 | A | G | | AA/AG |
| 6 | 11, 12 | A | G | | AA/AG |
| 7 | 13, 14 | A | G | | AA/AG |

Disclosed high yield sesame plants with shatter-resistant capsules were derived by computationally supported breeding methods to yield plants which are different and distinct from any prior art sesame varieties. Specifically, disclosed high yield sesame plants have QTL 4 in common and are grouped herein by combinations of QTLs denoted in Table 1 as cassette 1 and cassette 2.

FIGS. 2A-2C present experimental results indicating the correlation between phenotypic traits and the higher yield in sesame varieties with the disclosed marker cassettes, according to some embodiments of the invention. The total number of capsules directly influences the total yield and is shown to be correlated with the phenotypic traits—Number of lateral shoots (FIG. 2A), Height to first capsule (FIG. 2B). Additionally, Capsule length is shown to be correlated with total yield (FIG. 2C). The data were collected with breeding material that included the elite lines (e.g., sesame varieties ES103, ES107, ES108, of the 2019 harvest. FIGS. 2A-2C illustrate the corresponding bivariate normal ellipses for p=0.95. The significance of the relation between the yield and phenotypic traits was high, for example, in FIG. 2A, correlation coefficient of 0.73 between the yield and the Number of lateral shoots, with p<0.0001 for 2230 plants; in FIG. 2B, correlation coefficient of −0.36 between the yield and the Height to first capsule, with p<0.0001 for 446 plants; and in FIG. 2C, correlation coefficient of 0.39 between the yield and the Capsule length, with p<0.001 for 252 plants.

FIGS. 3A-3C present experimental results indicating the significant differences provided by the disclosed cassettes on overall yield in sesame, according to some embodiments of the invention. FIG. 3A illustrates the significant effect of QTL 4 (associated with the Number of capsules per leaf axil) on the total yield measured as total number of capsules. FIG. 3B illustrates the significant effect of cassette 1 markers on the yield (normalized with respect to the control commercial varieties grown under the same conditions and having the highest yield, including registered sesame lines ES103 and ES108) and FIG. 3C illustrates the significant effect of both cassettes (1 and 2) on the normalized yield.

In FIGS. 2A, 2B and 3A (with measured number of capsules on the y axis), each figure includes data points for single F2 plants. In FIGS. 2C, 3B and 3C (with measured yield on the y axis), each figure includes data points for groups of plants derived from self-crossed progeny of an older generation.

Advantageously, disclosed embodiments provide sesame plants with high yield that may make sesame growing profitable even in developed countries. Specifically, yield improvements of at least 10% with respect to control lines such as registered sesame lines ES103, ES107 and ES108 and up to three times the yield of the control lines.

QTL 1, as used herein, refers to a polymorphic genetic locus linked to genetic marker MaSI0003637 on sesame chromosome 9. The two alleles of marker MaSI0003637 at QTL 1 have the SNP bases "C" or "G", respectively, at position 6319255 (+strand) of Chr9, as set forth, respectively, in the nucleic acid sequences of SEQ ID Nos: 1 and 2. In cassette 1. QTL 1 may be homozygous for allele 1 (SEQ ID NO: 1) or be heterozygous (SEQ ID Nos: 1 and 2).

SEQ ID NO: 1 (SNP base bold):
CTATCTTTGTGATAATCCTATAAATTAAACAAAAATACCATTGACTATTGA

GATTAGAGAAAGATGCAATTTAACTCATCTAATATGAGAAATGAGTAAAAG

TGTTATGATAATTTGCTAATTCCTTTTTTGCACTGGTTTATCTGCTCATTT

CACATAT

SEQ ID NO: 2 (SNP base bold):
CTATCTTTGTGATAATCCTATAAATTAAACAAAAATACCATTGACTATTGA

GATTAGAGAAAGATGCAATTTAACTCATGTAATATGAGAAATGAGTAAAAG

TGTTATGATAATTTGCTAATTCCTTTTTTGCACTGGTTTATCTGCTCATTT

CACACTAT

QTL 2, as used herein, refers to a polymorphic genetic locus linked to genetic marker MaSI0003889 on sesame chromosome 6. The two alleles of marker MaSI0003889 at QTL 2 have the SNP bases "T" or "C", respectively, at position 14822546 (+strand) of Chr6, as set forth, respectively, in the nucleic acid sequences of SEQ ID NOs: 3 and 4. In cassette 1, QTL 2 may be homozygous for allele 1 (SEQ ID NO: 3) or be heterozygous (SEQ ID Nos: 3 and 4).

SEQ ID NO: 3 (SNP base bold):
AGTTTTTGTTCTTAAACAGTGCATTTTTTTTTTTTGACAAAATTCATTA

TTTTCATTATCTTGCTGTCAAATATAATGAAAAAATTCATCTGAGGCTGTT

TGAGGGTGGGAAAGAAAAACTATCATTTCCTCCCTGAAATTTAATTTTTTG

AATATTTAATCATATTCGGACAGGTGATATTTTCACATAAAAGCAAT

SEQ ID NO: 4 (SNP base bold):
AGTTTTTGTTCTTAAACAGTGCATTTTTTTTTTTTGACAAAATTCATTA

TTTTCATTATCTTGCTGTCAAATATAATGAAAAAATTCATCTGAGGCTGCT

TGAGGGTGGGAAAGAAAAACTATCATTTCCTCCTGAAAKTTTAATTTTTT

GAATATTTAATCATATTCGGACAGGTGATATTTTCACATAAAAGCAAT

QTL 3, as used herein, refers to a polymorphic genetic locus linked to genetic marker MaSI0003835 on sesame chromosome 9. The two alleles of marker MaSI0003835 at QTL 3 have the SNP bases "A" or "G", respectively, at position 12880820 (+strand) of Chr9, as set forth, respectively, in the nucleic acid sequences of SEQ ID Nos: 5 and 6. In cassette 1, QTL 3 may be homozygous for allele 1 (SEQ ID NO: 5) or be heterozygous (SEQ ID Nos: 5 and 6).

SEQ ID NO: 5 (SNP base bold):
AACACAAAAAACCAAACACTTTCATATGATCATAGTTAGGGGCCTTCTTAT

ATAATAATTCATAGGGTGTTTTCCAACTTAATGTTTGTGTTGGAAGTCTAT

TAATTATGTATGTGGCAGCTAACAATGCCTCGGCCCAGAATCTTTGTGGCA

TGTTTGCTTGGAACATCAAAGATCTAGCCCCTTGAAAAAGGTGTTGGT

SEQ ID NO: 6 (SNP base bold):
AACACAAAAAACCAAACACTTTCATATGATCATAGTTAGGGGCCTTCTTAT

ATAATAATTCATAGGGTGTTTTCCAACTTAATGTTTGTGTTGGAAGTCTGT

TAATTATGTATGTGGCAGCTAACAATGCCTCGGCCCAGAATCTTTGTGGCA

TGTTTGCTTGGAACATCAAAGATCTAGCCCCTTGAAAAAGGTGTTGGT

QTL 4, as used herein, refers to a polymorphic genetic locus linked to genetic marker MaSI0003448 on sesame chromosome 7. The two alleles of marker MaSI0003448 at QTL 4 have the SNP bases "T" or "C", respectively, at position 4339429 (+strand) of chromosome 7, as set forth, respectively, in the nucleic acid sequences of SEQ ID Nos: 7 and 8. In both cassettes 1 and 2, QTL 4 may be homozygous for allele 1 (SEQ ID NO: 7) or be heterozygous (SEQ ID Nos: 7 and 8).

SEQ ID NO: 7 (SNP base bold):
ATTTGGAGCCGGGTTCACATTGTTTCCAGCCTCTCAAAGGATTTTGGTCTT

CCAGGATTCAGGATCGGCATGATCTATTTCAACAGTAAAACCCTGATTGCT

GCTGCAACAAAAATGTCGAGTTTTGGGCTGGTCTCTTCTCAATCCCAGTTC

CTACTGT

SEQ ID NO: 8 (SNP base bold):
ATTTGGAGCCGGGTTCACATTGTTTCCAGCCTCTCAAAGGATTTTGGTCTT

CCAGGATTCAGGATCGGCATGATCTATTCCAACAGTAAAACCCTGATTGCT

GCTGCAACAAAAATGTCGAGTTTTGGGCTGGTCTCTTCTCAATCCCAGTTC

CTACTGT

QTL 5, as used herein, refers to a polymorphic genetic locus linked to genetic marker MaSI0003358 on sesame chromosome 3. The two alleles of marker MaSI0003358 at QTL 5 have the SNP bases "A" or "G", respectively, at position 3895479 (+strand) of Chr3, as set forth, respectively, in the nucleic acid sequences of SEQ ID NOs: 9 and 10. In cassette 2. QTL 5 may be homozygous for allele 1 (SEQ ID NO: 9) or be heterozygous (SEQ ID NOs: 9 and 10).

SEQ ID NO: 9 (SNP base bold):
TTAAAGTGATGAGAGTTGATGTTACTGAGAATATAAATGAGGATACTGTGA

AGCAGTTTATCGAAGAAGACAATGAGAACACAACCAGCAAGGACACCAAAG

AGGAAGTTACTGATATGGGTAACAATCAGCCAGATCGAGTTGCTGCACAAG

GAGATAATGATGTGATGGAAGATGAAAATAATTTAGACATGAAGC

SEQ ID NO: 10 (SNP base bold):
TTAAAGTGATGAGAGTTGATGTTACTGAGAATATAAATGAGGATACTGTGA

AGCAGTTTATCGAAGAAGACAATGAGAACACAACCAGCAAGGACACCGAAG

AGGAAGTTACTGATATGGGTAACAATCAGCCAGATCGAGTTGCTGCACAAG

GAGATAATGATGTGATGGAAGATGAAAATAATTTAGACATGAAGC

QTL 6, as used herein, refers to a polymorphic genetic locus linked to genetic marker MaSI0003838 on sesame chromosome 9. The two alleles of marker MaSI0003838 at QTL 6 have the SNP bases "A" or "G", respectively, at position 18953887 (+strand) of Chr9, as set forth, respectively, in the nucleic acid sequences of SEQ ID Nos: 11 and 12. In cassette 2. QTL 6 may be homozygous for allele 1 (SEQ ID NO: 11) or be heterozygous (SEQ ID NOs: 11 and 12).

SEQ ID NO: 11 (SNP base bold):
ATCATGAATTTTTACTCCTATTTTTTTGTTAATATTAACAAATCTAGTGGA

TTTTGACTAACAAAGGGACTTATTTTATTAAACGAAAAGCAACCTTCAAGG

ATATTAAATATAATTTTTCAAACCACATGAGATTTATATGCAATTACATTA

AATTTCGGTAGAGTGGAGTAGTTATCCCTAGAAATATTACAGTCGAAGTG

SEQ ID NO: 12 (SNP base bold):
ATCATGAATTTTACTCCTATTTTTTTGTTAATATTAACAAATCTAGTGGAT

TTTGACTAACAAAGGGACTTATTTTATTAAACGAAAGCAACCTTCAAGGGT

ATTAAATATAATTTTTCAAACCACATGAGATTTATATGCAATTACATTAAA

TTTCGGTAGAGTGGAGTAGTTATCCCTAGAAATATTACAGTCGAAGTG

QTL 7, as used herein, refers to a polymorphic genetic locus linked to genetic marker MaSI0003635 in linkage group 15 on sesame chromosome 9. The two alleles of marker MaSI0003635 at QTL 7 have the SNP bases "A" or "G", respectively, on the minus strand, at position 17947299 of Chr9, as set forth, respectively, in the nucleic acid sequences of SEQ ID NOs: 13 and 14. In cassette 2. QTL 7 may be homozygous for allele 1 (SEQ ID NO: 13) or be heterozygous (SEQ ID Nos: 13 and 14).

SEQ ID NO: 13 (SNP base bold):
GGAGGCAAAAGAATACGGGTTGGTTGATGCAGTGATCGATGATGGCAAGCC

TGGACTAGTCGCACCCATCGCAGATACTGCACCCCCACCAAAAACCCGTGT

CTGGGATCTTTGGAAAATCGAAGGCAGTAAAAAAGCCAAGAAAAACTTACC

CTCCGAAGAGAAACTATTACAAAATGGATACACAGTTGGCCAAGGTGAAGA

TGACAGAAGCACGGAACAGGTAGAGGAAGCACCAACATCTCAATGAGTAAT

GAATGTTGAGATATTTCTTGTATACACTGTCAAACATTGTAGCTAG

SEQ ID NO: 14 (SNP base bold):
GGAGGCAAAAGAATACGGGTTGGTTGATGCAGTGATCGATGATGGCAAGCC

TGGACTAGTCGCACCCATCGCAGATACTGCACCCCCACCAAAAACCCGTGT

CTGGGATCTTTGGAAAATCGAAGGCAGTAAAAAAGCCAAGAAAAACTTGCC

CTCCGAAGAGAAACTATTACAAAATGGATACACAGTTGGCCAAGGTGAAGA

TGACAGAAGCACGGAACAGGTAGAGGAAGCACCAACATCTCAATGAGTAAT

GAATGTTGAGATATTTCTTGTATACACTGTCAAACATTGTAGCTAG

High yield sesame plant(s) or part(s) thereof are provided, which have shatter-resistant capsules and comprise a plurality of loci associated with a corresponding plurality of quantitative trait loci (QTLs) having a corresponding plurality of nucleic acid genetic markers that are associated with a plurality of phenotypic traits of the sesame plant.

In certain embodiments, the phenotypic traits at least a Number of capsules per leaf axil trait, a Capsule length trait and a Height to first capsule trait.

The QTL and marker associated with the Number of capsules per leaf axil trait may comprise QTL 4 with corresponding markers set forth in SEQ ID NOs: 7 or 8.

In certain embodiments, the QTLs and markers associated with the Capsule length trait may comprise QTLs 1, 2, 3 with corresponding markers set forth in SEQ ID NOs: 1 or 2. SEQ ID NOs: 3 or 4. SEQ ID NOs: 5 or 6, respectively.

In certain embodiments, the QTLs and markers associated with the Height to first capsule trait may comprise QTLs 1, 3 with corresponding markers set forth in SEQ ID NOs: 1 or 2, SEQ ID NOs: 5 or 6, respectively.

In certain embodiments, the phenotypic traits may further comprise a Number of lateral shoots trait, and the QTL and marker associated with the Number of capsules per leaf axil trait may comprise QTL 3 with corresponding markers set forth in SEQ ID NOs: 5 or 6.

In certain embodiments, the QTLs and markers associated with the Capsule length trait, with the Height to first capsule trait and with the Number of lateral shoots trait—may comprise QTLs 5, 6, 7 with corresponding markers set forth in SEQ ID NOs: 9 or 10, SEQ ID NOs: 11 or 12, SEQ ID NOs: 13 or 14,—respectively.

In certain embodiments, the phenotypic traits may comprise a high yield of up to three times higher than the control variety (see, e.g., FIG. 3B). In various embodiments, the plants may be hybrids and/or the plant parts may comprise any of a seed, an endosperm, an ovule, pollen, cell, cell culture, tissue culture, plant organ, protoplast, meristem, embryo, or a combination thereof.

FIG. 4 is a high-level schematic illustration of a computationally supported breeding method 200, according to some embodiments of the invention. Computationally supported breeding method 200 is used to detect and combine QTLs from a plurality of sesame varieties to develop disclosed high yield sesame plants with shatter-resistant capsules which are different than any of the parent varieties by virtue of the achieved phenotypical and/or yield characteristics.

Computationally supported breeding method 200 comprises stages of trait discovery by growing and phenotyping a broad spectrum of varieties (stage 210), trait blending by developing hybridized lines through crossing the selected lines to mix and combine traits and selfing of the progeny in subsequent generations (stage 220), Target Product Genomic Code (TPGC) discovery by associating phenotypes and genotypes using derived linkage maps (stage 230), in silico validation to suggest candidate varieties (stage 240), breeding of the candidate varieties to identify varieties with the best TPGC potential (stage 250) and genomic code (GC) discovery to identify the most stable QTLs in hybridized progeny generation(s) (stage 260), as explained in detail below. TPGC discovery 230, in silico validation 250 and GC discovery 260 are based on computational algorithms that cannot be performed manually and provide the computational support for the judicious selection of the varieties that are generated and further crossed during the development process to yield disclosed high yield sesame plants with shatter-resistant capsules.

In certain embodiments, sesame lines were bred to reach high yield levels by collecting various sesame lines worldwide, creating F2 linkage populations, applying intensive phenotyping and genotyping of thousands of sesame lines, predicting of QTL's affecting the yield level trait, and establishing unique marker combinations, termed "marker cassettes" herein, to characterize novel high yield lines found by the methods described herein and not existing in commercial or natural lines.

The breeding methodology was based on algorithms for deriving the Target Product Genomic Code (TPGC) to associate (i) the Target Product (TP) being defined in advance based on market requirements and including a set of desired attributes (traits) that are available in natural genetic variations; and (ii) the Genomic Code (GC) comprising set(s) of genomic regions that include quantitative trait loci (QTLs) that affect and are linked to the TP traits. The algorithms may be configured to calculate multiple genomic interactions and to maximize the genomic potential of specific plants for the development of new varieties. The breeding program was constructed to derive the TPGC, and then by crossing and selfing to achieve a product which contains the specific GC that corresponds to the required TPs.

Certain embodiments of the breeding process of developing lines, through crossing and successive generations of selfing comprise stages such as: (i) Trait Discovery, in which a broad spectrum of varieties from different geographies and worldwide sources are grown and phenotyped in order to discover new traits that can potentially be combined to create a new product; (ii) Trait Blend, in which a crossing cycle is carried out based on phenotypic assumption(s), in which the different traits are mixed and combined. Initial trait cycle(s) are followed by additional cycle(s) to create F2 (and possibly higher generations) population(s) that provide the basis for algorithmic analysis for constructing the TPGC; (iii) TPGC Discovery, in which the plant(s) are phenotyped and genotyped to produce linkage map(s), discovering the relevant QTLs and deriving the TPGC; (iv) several line validation stages over several years in which sesame lines based on millions of in silico calculated variations (and/or selections) are grown and are used to defined the initial varieties; (v) Trait TPGC Blend, in which accurate crossings are performed in order to calculate the most efficient way to reach the best TPGC. The crossings are performed after in silico selection from millions of combinations, and are based, at least on part on phenotype assumptions; and (vi) Consecutive algorithm-based GC discovery stage(s) applied to F2 (or higher generation) population(s) grown in additional cycle(s).

Defining the TP for high yield shatter-resistant sesame varieties includes the development of high throughput methods for high yield level identification.

In the following non-limiting example of the process, Trait Discovery (i) was based on propriety germplasm including hundreds of elite varieties and thousands of F2 individual plants and also 219 different sesame lines that were obtained from the U.S. National Plant Germplasm System (NPGC) and courtesy of professor Amram Ashri sesame germplasm collection (see Ashri, A. 1998, Sesame Breeding. In: Janick J. (ed.), Plant Breeding Reviews Vol. 16. John Wiley and Sons, Somerset, N.J., pp. 179-228). These lines were used for the Trait Blend stage (ii), with crosses executed based on the potential for enrichment of genomic diversity to create new complex(es) of traits for the high yield level as the initial step for the TP-directed breeding program for high yield sesame lines. The resulting F1 hybrids were later self-crossed to create F2 linkage populations that showed phenotypic segregation. The F2 population were then planted in three different environments for discovering the TPGC (iii) that includes high yield traits. After screening and deep phenotyping of 2500 individuals, a set of ca. 300 representatives was selected. The selected individuals from the F2 population were further massively phenotyped for traits associated with yield, as detailed in the following. The measurement results were summarized into the representative high yield level trait.

TPGC Discovery (iii) included genotyping ca. 2500 selected individual plants from six populations. The Analysis was performed with a panel of 612 markers based on single nucleotide polymorphism (SNP) and directly designed based on the polymorphism found in the parental lines of the populations which were analyzed in depth using high throughput DNA sequencing technologies. The Panel was designed to maximize the chance to have the largest number of common segregate SNPs in order to create highly similar linkage maps for all observed populations. The computation of linkage maps was executed on each linkage F2 population based on the genotyping results. Linkage maps were computed with MultiPoint, an interactive package for ordering multilocus genetic maps, and verification of maps based on resampling techniques. Discovery of QTLs that are related to high yield level was carried out with the MultiQTL package, based on the linkage maps that were merged by Multipoint and the F2 population phenotype data, and using multiple interval mapping (MIM). MultiQTL significance was computed with permutation, bootstrap tools and FDR (false discovery rate) for total analysis. The linkage maps of all six F2 populations and the information of the high yield level traits over all genotyped plants belonging to those populations were analyzed and used to predict the QTLs in a "one trait to one marker" model, in which for all markers that constructed the linkage maps, each trait was tested independently against each one of the markers. In the provided examples, altogether seven markers were found to be related to yield and traits associated with yield components (see Table 1 above), with one marker common to all high yield populations.

In general, the six linkage F2 populations presented different markers that related to high yield levels. However, subsets of common markers were found to be shared by multiple populations and are referred to herein as marker cassettes. The significance and co-occurrences of the high yield level markers were evaluated using an algorithm that related the genotype-phase of each marker to respective QTLs and traits in linkage maps of the six F2 populations (also called "linkage F2 populations" herein) in each population, for populations in different environments. The occurrence of high yield level markers in two or more linkage maps of the F2 population (repetitive markers) strengthened its significance as representative for high yield level QTL.

It is emphasized that the breeding process is explained using non-limiting examples from a specific part of the breeding program, and is not limited to the specific populations and varieties derived by this specific part of the breeding program. For example, different F2 population may be bred and used to derive additional varieties that are characterized by one or more of the disclosed QTLs.

Following TPGC Discovery (iii), an in-silico breeding program (iv) was established to process the TPGC blend (including combinations of QTLs for different plants) to simulate and predict the genotypic states of self, cross-self and hybrid plant with respect to the QTLs and their predicted effects on each phase of the markers for the high yield level trait. The in-silico breeding program was constructed to yield millions of in silico selfing combinations which were bred and evaluated in-silico up to F8—to measure the potential for each of the genotyped plants to acquire the high yield level in the right combination at the right phase. The analysis resulted in identifying ca. 300 F2 plants having the highest score for high yield level, which were thus chosen for the actual selfing and cross-selfing procedures. The F3 seeds from these selected F2 plants were sown in plots in the subsequent growing season. Under this procedure. QTLs from different populations were combined to yield F3 plants containing new and unique cassettes of QTLs and yielding high yield levels.

The high yield sesame lines were then validated as retaining the trait in the following generations by genotyping the F3 and some subsequent generation offspring to verify they maintained the identified marker cassettes. Specifically, the parental lines of linkage F2 populations together with 220 different sesame cultivars (landraces and old commercial varieties) were genotyped based on high yield level markers of all populations. The cassettes detailed in Table 1 were found to wholly differentiate the developed high yield lines from the rest of the sesame cultivars screened.

EXAMPLES

Example 1

Breeding of High Yield Sesame Plants with Shatter-Resistant Capsules Having Cassette 1 (QTLs 1, 2, 3 and 4) and Cassette 2 (QTLs 5, 6, 7 and 4)

High yield sesame plants 100 with shatter-resistant capsules that were bred with computational support and comprise disclosed QTLs, according to some embodiments of the invention, of which non-limiting examples are provided in FIGS. 5A-5C.

FIG. 5A provides an example of breeding high yield sesame plants 100 with shatter-resistant capsules that have QTLs 1, 2, 3 and 4 of cassette 1, during six years and 18 computationally-supported breeding steps (denoted by date from Q1 of 2014 to Q3 of 2020), using parent varieties (denoted 174, 517, 181, 198, with respective introduced QTLs) and computationally-supported genomic and phenotypic selection. FIG. 5B provides an example of breeding high yield sesame plants 100 with shatter-resistant capsules that have QTLs 5, 6, 7 and 4 of cassette 2, during six years and 18 computationally-supported breeding steps (denoted by date from Q1 of 2014 to Q3 of 2020), using parent varieties (denoted 174, 517, 181, 91, with respective introduced QTLs) and computationally-supported genomic and phenotypic selection. FIG. 5C provides an example of breeding high yield sesame plants 100 with shatter-resistant capsules that have QTLs 1-7 of cassettes 1 and 2, during six years and 21 computationally-supported breeding steps (denoted by date from Q1 of 2014 to Q3 of 2020), using parent varieties (denoted 174, 517, 181, 91, 95, with respective introduced QTLs) and computationally-supported genomic and phenotypic selection. It is noted that the introduction of the QTLs from world varieties to yield disclosed varieties is similar in certain aspects to introgression of genetic matter from one species to another, but is carried out in the current invention at a lower taxonomical level, namely within the species level, introducing genetic material from several varieties of the same species to yield the disclosed varieties.

The inventors note that none of the high yield sesame plants 100 with shatter-resistant capsules that were bred according to the methods described herein is naturally occurring; indeed, they were derived by highly complicated computationally-supported breeding methods 200 described above, in which the genotypes of multiple sesame varieties were judiciously combined and analyzed, to discover and accumulate the recited QTL markers and corresponding phenotypic traits. Although the recited sesame plants are not genetically modified by sequences originating from other species, they cannot be reached merely by natural processes, as is evident by the detailed and intentional breeding program that was applied to specifically measure required characteristics, detect corresponding markers using bioinformatics methods and combine the detected QTLs in the selected varieties by classic breeding approaches. The inventors note that due to the huge complexity of the breeding program, involving growing, selecting and breeding of hundreds of varieties over many generations in the field, and based on genetic analysis of the varieties and of the relations of markers to phenotypic characteristics, this breeding process cannot happen merely by natural means and therefore cannot be considered a natural phenomenon. It is further noted that due to the shatter-resistance characteristics, disclosed varieties are severely hindered from natural plant propagation. Finally, it is noted that while the disclosed QTL markers are not heterologous to sesame as a species, the identified QTLs are not present in the recited combinations in any of over 200 prior art varieties which were used as initial breeding stock (see further data below), and that the QTLs genomics of the sesame plants has been significantly and judiciously modified by the breeding program. Therefore, at the taxonomic level of the varieties, the high yield sesame plants may be considered hybridized in that the QTL markers are mixed and introduced from other sesame varieties.

Example 2

Comparison of High Yield Shatter-Resistant Sesame Plant Varieties with World Varieties A comparison of 514 high yield shatter-resistant sesame plant varieties, according to some embodiments of the invention was made with 210 world varieties, as shown in FIGS. 6A-6C. The 514 disclosed high yield shatter-resistant sesame plant varieties are examples for sesame varieties that were derived by disclosed computationally supported breeding methods 200.

FIG. 6A illustrates schematically that none of the prior art varieties has the combination of QTL markers denoted herein as cassette 1 (QTLs 1, 2, 3 and 4), FIG. 6B illustrates schematically that none of the prior art varieties has the combination of QTL markers denoted herein as cassette 2 (QTLs 5, 6, 7 and 4), and FIG. 6C illustrates schematically that none of the prior art varieties has the combination of QTL markers in either cassette 1 or 2. Accordingly, disclosed high yield sesame plant varieties with shatter-resistant capsules are clearly and unequivocally distinct from any of the prior art varieties.

In the above description, an embodiment is an example or implementation of the invention. The various appearances of "one embodiment", "an embodiment". "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

Example 3

High Yield Sesame Plant 20-98002 with Shatter-Resistant Capsules Having Cassette 1 (QTLs 1, 2, 3 and 4) and Cassette 2 (QTLs 5, 6, 7 and 4)

Plant varieties 174 (QTLs 2 and 3), 517 (QTL 7), 181 (QTLs 3 and 6) and 198 (QTLs 2 and 7) were the source parents for hybridization. F2 populations and QTL discovery supported by computational support. Plant variety 174 had the associated phenotypes of strong seed retention and high yield, respectively. Plant variety 517 had the associated phenotypes of multiple branching. Plant variety 181 had the associated phenotypes of compact plant architecture, multiple branches and longer capsule, respectively. Plant variety 198 had the associated phenotypes of long capsule and early set of first capsule, respectively.

The aforementioned breeding, shown in FIG. 5C produced the following sesame plants 15-0063, 15-0589 and 15-0182 by genomic selection which led to selection of 15-0182 that comprises combination of 4 QTL together and having the following properties of compact plant architecture, stronger seed retention, multiple branches and higher yield potential. Varieties 91 and 95 having the following properties of 3 capsules per leaf axil and high yield potential.

The final product plant variety, named 20-98002 having Cassette 1 (QTLs 1, 2, 3 and 4) and Cassette 2 (QTLs 5, 6, 7 and 4) had higher yield of at least 10% than E103, 108, 107.

The invention is not limited to the accompanying diagrams or to their corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of certain embodiments. Other possible variations, modifications, and applications are also within the scope of the invention. Accordingly, the scope of the invention should not be limited by what has thus far been described, but by the appended claims and their legal equivalents.

---

What is claimed is:

1. A sesame plant with shatter-resistant capsules, progeny thereof or part(s) thereof; the sesame plant, progeny thereof or part(s) thereof comprising:
    a plurality of quantitative trait loci (QTLs) having a corresponding plurality of nucleic acid genetic markers that are associated with a plurality of phenotypic traits of the sesame plant; wherein the QTLs are combined in the sesame plant, progeny thereof or part(s) thereof from a plurality of sesame varieties by computationally supported breeding;
    wherein the phenotypic traits comprise at least a Number of capsules per leaf axil trait, a Capsule length trait, a Number of lateral shoots trait and a Height to first capsule trait; wherein the QTL associated with the Number of capsules per leaf axil trait comprises QTL 4 with markers of SEQ ID NO: 7 and SEQ ID NO:8, and the sesame plant, progeny thereof or part(s) thereof is homozygous with respect to SEQ ID NO: 7; wherein the QTLs associated with the Capsule length trait comprise QTL 1 with markers of SEQ ID NO: 1 and SEQ ID NO:2, QTL2 with markers of SEQ ID NO: 3 and SEQ ID NO:4, and QTL3 with markers of SEQ ID NO: 5 and SEQ ID NO:6; and wherein the QTLs associated with the Height to first capsule trait comprise QTLs 1 and 3, and the sesame plant, progeny thereof or part(s) thereof is homozygous with respect to SEQ ID NO: 1, SEQ ID NO: 3, and SEQ ID NO: 5.

2. A sesame plant with shatter-resistant capsules, progeny thereof and/or or part(s) thereof; the sesame plant, progeny thereof or part(s) thereof comprising:
    a plurality of quantitative trait loci (QTLs) having a corresponding plurality of nucleic acid genetic markers that are associated with a plurality of phenotypic traits of the sesame plant; wherein the QTLs are combined in the sesame plant, progeny thereof or part thereof from a plurality of sesame varieties by computationally supported breeding;
    wherein the phenotypic traits comprise at least a Number of capsules per leaf axil trait, a Capsule length trait, a Number of lateral shoots trait and a Height to first capsule trait; wherein the QTL associated with the Number of capsules per leaf axil trait comprises QTL 4 with markers of SEQ ID NO: 7 and SEQ ID NO:8, and the sesame plant, progeny thereof or part(s) thereof is homozygous with respect to SEQ ID NO: 7; and wherein the QTLs associated with the Capsule length trait, the Height to first capsule trait and the Number of lateral shoots trait comprise QTL 5 with markers of SEQ ID NO: 9 and SEQ ID NO:10, QTL6 with markers of SEQ ID NO: 11 and SEQ ID NO:12, and QTL7 with markers 13 and SEQ ID NO:14, and the sesame plant, progeny thereof or part(s) thereof is homozygous with respect to SEQ ID NO: 9, SEQ ID NO: 11, and SEQ ID NO: 13.

3. A sesame plant with shatter-resistant capsules, progeny thereof or part(s) thereof, the sesame plant, progeny thereof or part(s) thereof comprising:
a plurality of quantitative trait loci (QTLs) having a corresponding plurality of nucleic acid genetic markers that are associated with a plurality of phenotypic traits of the sesame plant, wherein the QTLs are combined in the sesame plant, progeny thereof or part(s) from a plurality of sesame varieties by computationally supported breeding;
wherein the phenotypic traits comprise at least a Number of capsules per leaf axil trait, a Capsule length trait, a Number of lateral shoots trait and a Height to first capsule trait; wherein the QTL associated with the Number of capsules per leaf axil trait comprises QTL 4 with markers of SEQ ID NO: 7 and SEQ ID NO: 8, and the sesame plant, progeny thereof or part(s) thereof is homozygous with respect to SEQ ID NO: 7.

4. The sesame plant, progeny thereof or part(s) thereof according to claim 1, wherein the phenotypic traits further comprise a yield of at least ten percent more than control sesame lines ES103, ES107 and ES108.

5. The sesame plant, progeny thereof or part(s) thereof according to claim 1, wherein the part(s) thereof comprise any of: a seed, an endosperm, an ovule, pollen, cell, cell culture, tissue culture, plant organ, protoplast, meristem, embryo, or a combination thereof.

6. The sesame plant, progeny thereof or part(s) thereof according to claim 2, wherein the phenotypic traits further comprise a yield of at least ten percent more than control sesame lines ES103, ES107 and ES108.

7. The sesame plant, progeny thereof or part(s) thereof according to claim 2, wherein the part(s) thereof comprise any of: a seed, an endosperm, an ovule, pollen, cell, cell culture, tissue culture, plant organ, protoplast, meristem, embryo, or a combination thereof.

8. The sesame plant, progeny thereof or part(s) thereof according to claim 3, wherein the phenotypic traits further comprise a yield of at least ten percent more than control sesame lines ES103, ES107 and ES108.

9. The sesame plant, progeny thereof or part(s) thereof according to claim 3, wherein the part(s) thereof comprise any of: a seed, an endosperm, an ovule, pollen, cell, cell culture, tissue culture, plant organ, protoplast, meristem, embryo, or a combination thereof.

* * * * *